(12) United States Patent
Buzdin et al.

(10) Patent No.: US 11,614,434 B2
(45) Date of Patent: Mar. 28, 2023

(54) GENETIC INFORMATION ANALYSIS PLATFORM ONCOBOX

(71) Applicant: Obschestvo s ogranichennoi otvetstvennostyu "Oncobox", Moscow (RU)

(72) Inventors: Anton Alexandrovich Buzdin, Istra (RU); Maksim Igorevich Sorokin, Balashikha (RU); Viktor Sergeevich Tkachev, Moscow (RU); Daniil Mikhailovich Nikitin, Orel (RU); Marianna Arsenovna Zolotovskaya, Rostov-na-Donu (RU); Andrey Vladimirovich Garazha, Moscow (RU); Nikolai Mikhailovich Borisov, Krasnoznamensk (RU)

(73) Assignee: MICSWAY CORP., Claymont, DE (US)

( * ) Notice: Subject to any disclaimer, the term of this patent is extended or adjusted under 35 U.S.C. 154(b) by 1219 days.

(21) Appl. No.: 16/088,446

(22) PCT Filed: Mar. 1, 2018

(86) PCT No.: PCT/RU2018/000120
§ 371 (c)(1),
(2) Date: Sep. 26, 2018

(87) PCT Pub. No.: WO2019/168426
PCT Pub. Date: Sep. 6, 2019

(65) Prior Publication Data
US 2020/0292515 A1  Sep. 17, 2020

(51) Int. Cl.
*G01N 33/15* (2006.01)
*G16H 10/40* (2018.01)
*G16B 50/30* (2019.01)

(52) U.S. Cl.
CPC .............. *G01N 33/15* (2013.01); *G16B 50/30* (2019.02); *G16H 10/40* (2018.01)

(58) Field of Classification Search
CPC .......... G01N 33/15; G16B 50/30; G16B 5/30; G16H 10/40
(Continued)

(56) References Cited

U.S. PATENT DOCUMENTS

| 8,367,340 B2 * | 2/2013 | Carrier | C12Q 1/686 |
| | | | 435/6.12 |
| 2010/0173301 A1 * | 7/2010 | Carrier | C12Q 1/686 |
| | | | 435/6.14 |

(Continued)

FOREIGN PATENT DOCUMENTS

| CN | 104011726 A * | 8/2014 | ......... G06F 16/2219 |
| WO | WO-2004026109 A9 * | 6/2004 | ......... C12Q 1/6886 |
| WO | WO-2013062505 A1 * | 5/2013 | ......... G06F 16/2219 |

OTHER PUBLICATIONS

Jahja, Ermira; Investigation of Novel RNAi and Nanoparticle Approaches for Their Anti-proliferative and DrugSensitizing Effects in Breast Cancer; Bilkent Universitesi (Turkey), ProQuest Dissertations Publishing, 2017. 29046319 (Year: 2017).*

(Continued)

*Primary Examiner* — Hiep V Nguyen
(74) *Attorney, Agent, or Firm* — Nixon & Vanderhye PC

(57) ABSTRACT

The invention describes the method allowing for efficient predictive ranking of clinical efficiencies of the existing targeted medicinal products for individual patient with proliferative or oncology disease. The method makes it possible to use a wide range of experimental data received from the patients' pathological tissue samples and relevant control samples: information on gene mutations, transcription factor binding profile, protein (considering harmonization), mRNA (considering harmonization) and microRNA expression (Continued)

strength. The method also uses information on molecular targets of the medicinal products. This method can be automated to prevent potential errors associated with manual calculation and makes it possible to consider patient-specific changes in hundreds and thousands molecular pathways which include tens and hundreds of gene products. This method also considers the features and mode of action of various classes of target drugs. Using this method will enable selecting a medicinal product for the patient based on the analysis of objective individual changes occurred in the pathological tissue.

14 Claims, 10 Drawing Sheets

(58) Field of Classification Search
USPC .......................................................... 705/2
See application file for complete search history.

(56) References Cited

U.S. PATENT DOCUMENTS

| | | | |
|---|---|---|---|
| 2016/0132632 A1 | 5/2016 | Zavoronkovs et al. | |
| 2016/0132641 A1* | 5/2016 | Kupershmidt | G16B 20/10 707/723 |
| 2016/0224738 A1 | 8/2016 | Zhavoronkov et al. | |
| 2016/0224739 A1 | 8/2016 | Zhavoronkov et al. | |
| 2017/0193176 A1 | 7/2017 | Borisov et al. | |
| 2017/0262576 A1 | 9/2017 | Buzdin et al. | |
| 2017/0262578 A1 | 9/2017 | Buzdin et al. | |
| 2017/0277826 A1* | 9/2017 | Ozerov | G16B 25/00 |
| 2020/0143948 A1* | 5/2020 | Kamali-Zare | G06T 7/0016 |

OTHER PUBLICATIONS

Soumyanarayanan, Uttara; Epigenetic Targeted Drug Discovery: Inhibitors of Methyltransferase G9a and Dual Inhibitors of G9a and HDAC; National University of Singapore (Singapore). ProQuest Dissertations Publishing, 2016. 10907357 (Year: 2016).*
Huff, Sarah' Structure-Guided Synthesis and Evaluation of Non-Nucleoside Reversible, Competitive Inhibitors of Human Ribonucleotide Reductase as Anti-Proliferative Agents; : Case Western Reserve University. ProQuest Dissertations Publishing, 2017. 28079052 (Year: 2017).*
Borisov N, et al. "Data aggregation at the level of molecular pathways improves stability . . .". Cell Cycle. Oct. 2, 2017;16(19):1810-1823.
Aliper, Alexander, et al. "Mathematical Justification of Expression-Based Pathway Activation Scoring (PAS)." Methods in Molecular Biology (Clifton, N.J.), 2017, 1613:31-51.
Artemov A, et al. Oncotarget. Oct. 6, 2015;6(30):29347-56.
Buzdin, Anton A, et al. Bioinformatics Meets Biomedicine: "OncoFinder, a Quantitative Approach for Interrogating Molecular Pathways", Methods Mol Biol. 2017 (1613): 53-83.
Buzdin, Anton A, et al. "Oncofinder, a New Method for the Analysis of Intracellular Signaling Pathway Activation" Frontiers in Genetics, Mar. 25, 2014;5:55.
Ozerov IV, et al. "In silico Pathway Activation Network Decomposition Analysis (iPANDA) as a method ". Nat Commun. Nov. 16, 2016;7:13427.

* cited by examiner

GENETIC INFORMATION ANALYSIS PLATFORM ONCOBOX

This application is the U.S. National Phase of International Application No. PCT/RU2018/000120 filed on Mar. 1, 2018, the entire contents of each of which are hereby incorporated herein by reference.

FIELD OF THE INVENTION

The invention belongs to the personalized medicine for oncological diseases, namely to the clinical decision support system with the use of intracellular molecular pathways activity analysis based on large-scale mutation profiles and gene expression data.

BACKGROUND

The oncological diseases are characterized by cell cycle dysfunction, appearance of uncontrolled proliferating cells capable of rapid growth and invasion into the tumour-adjacent zones and metastatic spreading to remote tissues and organs. The oncological diseases occupy the leading positions among the causes of death in the industrial developed countries. Due to development of modern approaches to radiological and chemotherapy of cancer, as well as emergence of early detection techniques and metastasectomy methods improvement, in recent the decade the rate of mortality from such diseases tended to stabilize.

Today, more than 200 medicinal products and significantly bigger number of their combinations have been developed and are used in the clinical practice to treat cancer [https://www.cancer.gov/about-cancer/treatment/drugs]. But the problem of the right therapy selection for an individual patient remains largely unsolved. It is known that using the same drug for the same histo-morphological group of tumour patients can cause very different individual effects varying from complete tumour response to its further progression. This response cannot be predicted only on the basis of the case history and histological type of tumour, that is why today the therapy is frequently selected on the random basis from the list of drugs approved for the given type of cancer that is often associated with low efficiency of the therapy and high mortality rate.

The development of modern knowledge-intensive technologies for next generation sequencing (or deep sequencing) and transcriptome microarray techniques provided an instrument for a new type of analysis of the histologically homogeneous tumours. It was found out that the same histo-morphological status of a tumour can be associated with variable sets of molecular markers such as mutations and different gene expression profiles. Thus, in the current medicine, the information about histo-morphological type of tumour needs to be reinforced with the tumour genetics data when selecting the therapy. This approach is becoming more and more common in the modern clinical practice and has its obvious proven advantages (Martel C L, Lara P N. Renal cell carcinoma: current status and future directions. Crit Rev Oncol Hematol. 2003 February; 45(2):177-90).

On May 23, 2017, the US Food and Drug Administration (FDA) for first time ever approved the tumour genetic marker but not tumour localization or type as the indication for the use of an anti-cancer medicinal product Keytruda (Pembrolizumab) [https://www.fda.gov/NewsEvents/Newsroom/PressAnnouncements/ucm560167.html]. This trend suggests that the personalized oncology in the future may become a new standard of care. The relevant task, therefore, is to develop new generation of biomedical platforms enabling smart selection of the most efficient therapy and search for prognostic tumour markers for an individual patient. Wide implementation of such techniques in future will hopefully result in decrease of mortality from oncological diseases.

Now there is a limited number of diagnostic platforms utilizing specific kinds of large-scale genetic data for doctors' and patients' consulting. For example, in Caris Molecular Intelligence system (Russell et al. 2014; Green et al. 2014; Popovtzer et al. 2015; Vigneswaran et al. 2016), the use of a platform is based on the analysis of a limited spectrum of mutations with previously demonstrated clinical significance, and on the immunohistochemical profiling of the patients' biosamples for detection of few cancer protein biomarkers. Nevertheless, the above mentioned system does utilize the high throughput gene expression data, does not consider the molecular pathways activation and overall lacks the ability of multi-omics data processing. As a consequence, the potentials of such systems for the usage of multi-omics data for development of clinically significant recommendations are strongly limited.

The level of measuring intracellular molecular pathway activation requires data on concentrations of the gene products involved in this pathway.

The following methods had been developed before for measuring the molecular pathway activation: TAPPA (Gao and Wang 2007), topology-based score (TB) (Ibrahim et al. 2012), Pathway-Express (PE) (Draghici et al. 2007), SPIA (Tarca et al. 2009), Oncofinder (Buzdin et al., 2013), IPANDA (Ozerov et al., 2016) and others. These approaches use various formulae for calculation of the activation strength of the molecular pathways, that use data on the differential expression of genes participating in molecular pathways, as compared to control samples.

For example, the patent application US20170262578A1 describes estimation of molecular pathway activation (Pathway Activation Strength, PAS) according to the formula:

$$PAS_p = \sum_n ARR_{np} \cdot BTIF_n \cdot \lg(CNR_n)$$

Where $PAS_p$ is a molecular pathway activation strength p; $ARR_{np}$—gene product role n in a molecular pathway p (takes values from −1 to 1 depending on whether the gene product is a molecular pathway repressor or activator, respectively); $BTIF_n$ indicates if the gene product n is differentially expressed compared to the control sample group; lg—decimal logarithm; case-to-normal ratio, $CNR_n$—case to normal ratio of gene n equal to ratio of its expression level in the sample under investigation to the averaged expression level in control group. This algorithm was initially proposed for processing expression data of messenger RNA (mRNA) and also for protein expression profiles. The application of the pathway activation strength values can be development of next-generation biomarkers, as the PAS values can label various physiological and pathological states of cells, tissues and of the whole organism. The PAS values can be calculated for the pathological tissues of a patient. In case of oncological disease, this may be, for example, fresh biopsy tissue or formalin fixed, paraffin-embedded (FFPE) tumour tissue block.

The patent application US20160224739 A1 discloses a method of using a set on indices for molecular pathway activation to predict the response of the patients with breast cancer to different types of chemotherapy. To achieve this goal, for each type of chemotherapy covered by this assay, a reference set of marker PAS values is collected for the groups of patients-responders and non-responders to the respective treatment. After that, for the test case, a tissue biosample is investigated to obtain gene expression data (for example, using FFPE tumour tissue sample), the marker molecular pathway activation levels are measured and their activation profile is compared with the groups of responders and non-responders. Based on similarities of the marker pathway activation profiles in a patient under investigation with the responder or non-responder groups, the response of an individual patient to the specific chemotherapy treatment is predicted.

On the other hand, the patent application US20170193176A1 (see also the article by Artemov et al., 2015) discloses the method for calculating the relative drug efficiency (Drug Score, DS) based on the molecular pathway activation values. The authors propose the following formula to calculate DS:

$$DS_d = \Sigma_t DTI_{dt} \Sigma_p NII_{tp} AMCF_p PAS_p,$$

where DS is a predicted targeted drug efficiency; d is a specific targeted anticancer drug, whose efficiency is analysed; PAS is molecular pathway activation strength for a pathway p; $AMCF_p$ is a Boolean index considering the pathway p ability to strengthen or weaken the cell growth or death (it takes values 1 and −1, accordingly); DTI is an index considering the drug d ability to inhibit the gene product t or not (it takes values 1 and 0, respectively); NII is an index considering whether gene product t is involved in the molecular pathway p or not (it takes values 1 and 0, respectively).

However, as distinguished from the OncoBox system, the previous methods don't consider the change(s) in the efficient concentration(s) of molecular target(s) of the drugs under consideration. Another distinction is that the methods proposed in the applications US20170193176A1 and US20160132632A1 can analyse only the mRNA and protein expression data but not the DNA mutation data and/or data on distribution of transcription factor binding sites and data on concentrations of microRNAs.

Several important limitations apply to all the previously published methods of drug efficiency prediction.

First, they cannot simultaneously use a wide range of multi-omics genetic profiling results: information on gene mutations, transcription factor binding profiles, protein, mRNA and microRNA expression data. The methods of nominal prediction of the efficiencies of a large number of targeted anticancer drugs with different specificities in one test had never been published before based on high throughput gene mutation data, microRNA expression and transcription factors binding profiles.

Secondly, the previously published methods of drug efficiency prediction did not use a the measure the combination of the molecular pathway activation values and the individual quantitative metrics of gene changes (expression change or mutation burden) for the direct molecular targets of the drugs under consideration.

Third, the previously published approaches to mRNA and protein expression analysis did not solve the problem of data harmonization when combining the expression profiles of the test samples and of a set of normal (control) samples.

Fourth, during the analysis of molecular pathway activation, in the previous methods the role of each gene product in a pathway was determined by manual curation of the molecular pathway graph by an investigator. This is an apparent source of inevitable operational errors that restricts a wide use of such techniques due to impossibility of efficient manual processing of hundreds and thousands of molecular pathways, including each tens or hundreds of gene products forming numerous functional nodes.

Fifth, the previously published targeted drug parallel screening method algorithms poorly distinguished the nature of different classes of target drugs and their modes of action.

Today, in the clinical practice there is no efficient methods for prediction of the efficiencies of the existing anti-cancer arget drugst for an individual patient that would consider the individual peculiarities of the molecular imbalance occurred during development of the particular tumour. As a result, most of the patients receive standard medicinal treatments which are selected based on only clinical or morphological parameters, such as stage of cancer, tumour size, disease invasiveness and so on, that often leads to the lack of patients' response to the therapy and further tumour growth. Development of the personalized approach to cancer treatment based on the profound analysis of molecular dysfunction in the patient's organism is a relevant task, and this invention is aimed at expansion of a range of approaches applied to solve this objective.

SUMMARY OF THE INVENTION

The objective of the present invention is to create efficient, scientifically justified approach to the personalized therapy for oncological patients, that is to perform selection of anti-cancer drugs that are most suitable for an individual patient and capable of modulating the molecular pathways to compensate pathological changes in tumour tissues. The approach described in the present invention consists in the analysis of changes in intracellular molecular pathways: signalling, DNA repair, metabolic, cytoskeleton rearrangement and others, as well as prediction of clinical efficiencies of targeted drugs for individual oncological patients. The Oncobox platform described in the current invention will solve the objective of repurposing of the existing targeted drugs for new indications, as well as may solve the objective of finding efficient molecular targets during the development of new targeted medicinal products.

As the initial data, Oncobox uses the multi-omics genetic data obtained from the cell or tissue samples of the individual patients, and of the healthy individuals taken as the controls. The fresh tissue, FFPE tissue blocks or otherwise preserved tissue samples are used as the starting biomaterials. The sources of primary genetic data for Oncobox platform can be different multi-omics profiling data: at the mRNA level, high-throughput gene expression profiling with microarray hybridization or deep sequencing, or real-time reverse transcription PCR (RT-PCR); at the protein level, high throughput protein expression profiling using quantitative proteomic technologies; at the microRNA level, quantitative profiling of microRNA transcriptome; at the DNA mutation level, deep sequencing of genomic DNA, including exome sequencing; at the level of transcription factor binding sites, chromatin immunoprecipitation sequencing (ChIP-seq) or other relevant techniques.

Based on the multi-omics profiling results, the Oncobox platform estimates the extents of intracellular molecular pathway activation, and then estimates for an individual patient potential efficiencies of anticancer drugs with known spectra of molecular specificities.

The objective specified will be solved by using the method of defining the clinical efficiencies of targeted anti-cancer medicinal products for the treatment of proliferative disorder or oncological patients; the procedure includes at least the following stages: (a) receiving information about molecular targets for each targeted medicinal product selected from the group specified; (b) receiving the patient tissue sample with oncological or proliferative phenotype; (c) receiving molecular genetic data of at least one type for the specified biosample, and the data type will be selected from the following list: (i) total mRNA expression data, (ii) high throughput protein expression data, (iii) genome-wide data on transcription factor binding sites, (iv) genome-wide mutations data within genomic DNA, including exome sequencing data, (v) high throughput microRNA expression data;

(d) receiving data from at least one control tissue sample without oncological or proliferative phenotype, wherein the control sample is taken from the tissue of the same type as the specified patient's tissue, and the control sample data type matches the data type received at stage (c);

(e) receiving of at least one type of data on molecular targets for each targeted medicinal product from the specified sample, and the data type is selected from the following list: (i) mRNA molecular target expression data, (ii) molecular target expression data at the protein level, (iii) molecular target gene mutations data, (iv) transcription factor binding site data for molecular target genes, (v) expression data for microRNAs affecting the molecular target gene expression, wherein each data type (i)-(v) received at stage (e) matches the data type, respectively (i)-(v), received at stage (c);

(f) receiving molecular target data for each targeted medicinal product from at least one control tissue sample without oncological or proliferative phenotype, wherein the control sample is taken from the tissue of the same type as the patient's specified tissue, and the control sample data type matches the data type received at the stage (e);

(g) defining the quantitative indicators of the product efficiency for each data type (i)-(v) using data received at the stages (c)-(f);

(h) defining the clinical efficiency for each targeted medicinal product from the targeted medicinal products' group using the average efficiency quantitative indicators defined at stage (g).

In some preferred embodiments of the method, the disclosed above method of defining the clinical efficiency of targeted medicinal products is characterized by that the data obtained from at least one control tissue sample are harmonized with the data obtained at stages (c) and (e). In other embodiments, the method is characterized by (i) receiving data of at least two types at stage (c); (ii) calculating the efficiency quantitative indicator for each data type at stage (g); and (iii) calculating the clinical efficiency for each targeted medicinal product from the targeted medicinal products group by averaging the calculated efficiency quantitative indicators for each data type. In particularly preferred embodiments, they receive the genome-wide harmonized gene expression data and genome-wide or exome-wide mutations data at stage (c).

In other embodiments, the specified objective is solved by using the proliferative or oncological patient treatment method consisting of the following stages of at least: (a) receiving information about the available targeted medicinal products and creating a group of targeted medicinal products; (b) defining the clinical efficiency of the targeted medicinal products selected from the specified targeted medicinal products' group according to the disclosed above method of defining the clinical efficiency of the targeted medicinal products; (c) selecting a medicinal product with the best or one of the best efficiency quantitative indicators for the specified patient treatment defined according to the above method of defining the clinical efficiency of the targeted medicinal products.

In other embodiments, the specified objective is solved by using the clinical efficiency ranking system for targeted medicinal products selected from the targeted medicinal products group for a patient with tissue proliferative or oncological decease, including:

at least, one processing unit;

at least, one storage memory comprising machine-readable instructions which, when followed by at least one processing unit, define the clinical efficiency of the specified targeted medicinal products using the computer implemented method consisting, at least, of the following stages: (a) receiving information about molecular targets for each targeted medicinal product selected from the specified group; (b) receiving data of at least one type from the patient's tissue sample with oncological or proliferative phenotype, wherein the data type will be selected from the following list: (i) high throughput mRNA expression data, (ii) high throughput protein expression data, (iii) high throughput transcription factor binding site data, (iv) high throughput genomic DNA mutation data including exome mutation DATA, (v) high throughput microRNA expression data; (d) receiving data from at least one control tissue sample without oncological or proliferative phenotype, wherein the control sample is taken from the tissue of the same type as the specified patient's tissue, and the control sample data type matches the data type received at stage (c); (e) receiving of at least one type data on molecular targets for each targeted medicinal product from the specified sample, and the data type is selected from the following list: (i) molecular target mRNA expression data, (ii) molecular target protein expression data, (iii) molecular target gene mutations data, (iv) transcription factor binding site data for molecular target genes, (v) expression data for microRNAs affecting the expression of molecular target genes, wherein each of the data type (i)-(v) obtained at stage (e) matches the data type, respectively (i)-(v), received at stage (c); (f) receiving molecular target data for each targeted medicinal product from at least one control tissue sample without proliferative phenotype, wherein the control sample is taken from the tissue of the same type as the specified patient's tissue; the control sample data type matches the data type received at stage (e); (g) defining the quantitative indicators of the product efficiency for each data type (i)-(v) using data received at stages (c)-(f); (h) defining the clinical efficiency for each targeted medicinal product from the targeted medicinal products group using the average efficiency quantitative indicators defined at stage (g).

In other embodiments, the specified objective is solved by using the method of defining the most effective medicinal product from the targeted medicinal products group for a proliferative or oncology patient consisting of the following stages at least: (a) receiving information about molecular targets for each targeted medicinal product selected from the group specified; (b) receiving the patient tissue sample with proliferative phenotype; (c) receiving data of at least one type of the specified sample, and the data type will be selected from the following list: (i) high throughput mRNA expression data, (ii) high throughput protein expression data, (iii) high throughput transcription factor binding site data, (iv) high throughput genomic DNA mutation data including exome mutation DATA, (v) high throughput microRNA expression data; (d) receiving data from at least one control tissue sample without oncological or proliferative phenotype, wherein the control sample is taken from the tissue of the same type as the specified patient's tissue, and the control sample data type matches the data type received at stage (c); (e) receiving of at least one type data on molecular targets for each targeted medicinal product from the specified sample, and the data type is selected from the following list: (i) molecular target mRNA expression data, (ii) molecular target protein expression data, (iii) molecular target gene mutations data, (iv) transcription factor binding site data for molecular target genes, (v) expression data for microRNAs affecting the expression of molecular target genes, wherein each of the data type (i)-(v) received at stage (e) matches the data type, respectively (i)-(v), received at stage (c); (f) receiving molecular target data for each targeted medicinal product from at least one control tissue sample without oncological or proliferative phenotype, wherein the control sample is taken from the tissue of the same type as the specified patient's tissue; the control sample data type matches the data type received at stage (e); (g) defining the quantitative indicators of the product efficiency for each data type (i)-(v) using data received at stages (c)-(f); (h) defining the clinical efficiency for each targeted medicinal product from the targeted medicinal products group using the average efficiency quantitative indicators defined at stage (g).

The following technical effect is achieved in reduction to practice: development of a new, more effective method of defining the clinical efficiencies of targeted medicinal products for individual patient with tissue proliferative or oncological disease using a wide range of experimental data: data on gene mutations, on transcription factors binding profiles, in protein (considering harmonization), mRNA (considering harmonization) and microRNA expression strength, as well as molecular target information for targeted medicinal products. This method can be automated to prevent potential errors associated with manual calculation and makes it possible to consider changes in hundreds and thousands molecular pathways which include tens or hundreds of gene products being specific for a certain patient.

DETAILED DESCRIPTION OF THE INVENTION

Figure 1:
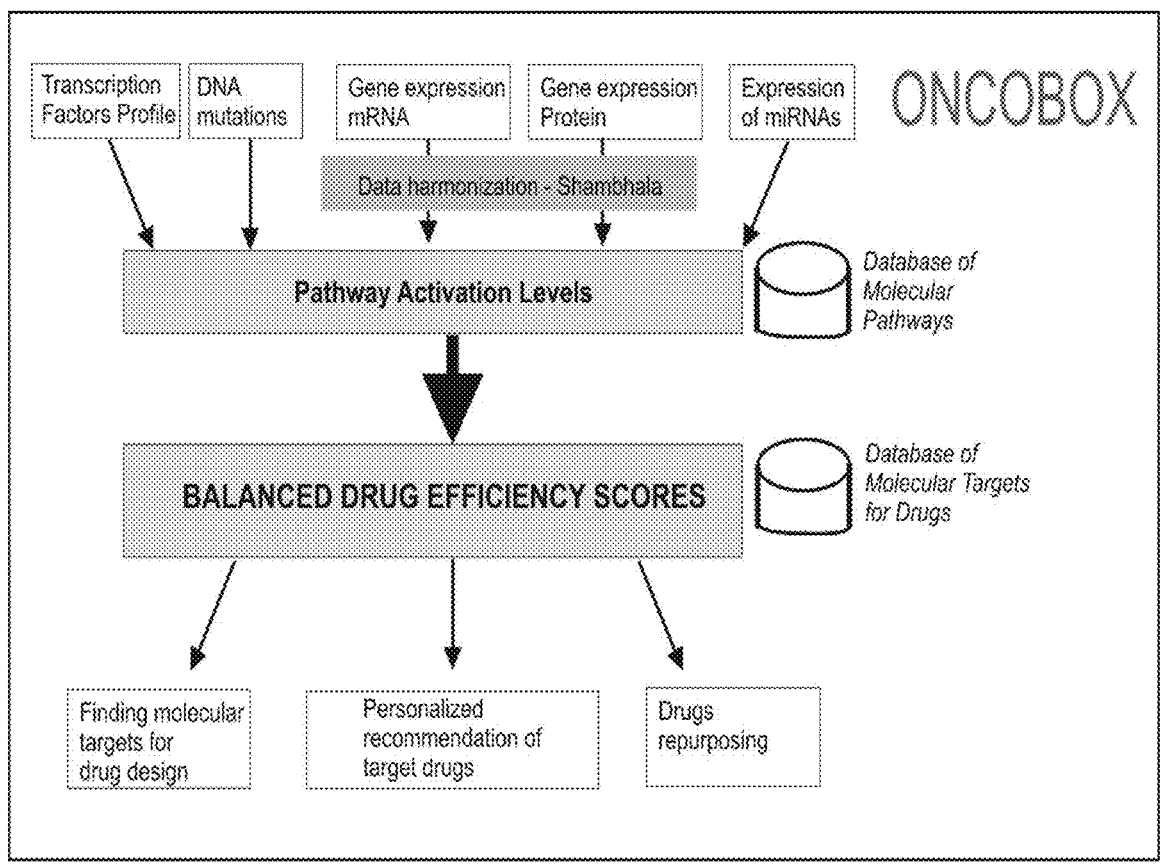
FIG. 1. Diagram of Oncobox platform organization.

In the description of the invention, the terms "includes" and "including" should be interpreted as "includes among others". These terms are not to be interpreted as "consists only of".

"Subject" or "patient" means a human (preferably) or any other mammal. Patient's or subject's "tissue" has a usual meaning adopted in the medical literature, i.e. a system of cells and intercellular substance having common origin, structure and functions. In description of this invention, this may refer to the blood, solid tissue of various origin (for example, epithelium, connective, nerve or muscular) or a part of any organ of the patient or subject.

A patient's tissue sample with proliferative phenotype means a tumour tissue sample with the cells capable of uncontrolled proliferation caused by a pathological change or by a group of pathological changes (usually, caused by mutations in genomic DNA). Such sample can be a part of benign or malignant tumour.

Proliferative or oncological disease means a disease characterized by pathological change in cell genetic system leading to uncontrolled proliferation of its progeny. The examples of proliferative disorders may be myeloproliferative diseases, lymphoproliferative diseases, proliferative diseases of connective tissue and other diseases including cancers.

Total mRNA expression data means data showing absolute or relative contents of all or over 300 kinds of mRNA molecules in a sample. Genome-wide transcription factor binding site data means data showing binding areas of the specified transcription factor set with DNA sequence in a subject's genome. This set is defined by a specialist based on transcription factors involvement in molecular pathways which are supposed to be linked with disease. The high throughput protein expression data, genome-wide and exome-wide mutations data within genomic DNA, and genome-wide microRNA expression data are defined in the same way.

Data harmonization means bringing expression data to the universal comparable mode. In the embodiment of this invention, harmonization is necessary for the use of total mRNA expression data or high throughput protein expression data when joining the testing sample patient's data with the relevant control sample(s), including those obtained using different experimental platforms. In such case, the Shambhala method described here or any other method enabling comparison of high throughput expression data obtained with different experimental platforms can be used for harmonization. When the patient's and control sample data are obtained using the same experimental platform, the data are considered harmonized without using additional algorithms. Similarly, for genome-wide mutations data, high throughput microRNA expression data and transcription factor binding site data, there is no need in harmonization, and such data are considered harmonized without using additional algorithms.

Unless otherwise defined, the technical and scientific terms in this description have standard meanings commonly used in scientific and technical literature.

The Oncobox platform solves the objectives for prediction of clinical efficiency of medicinal products for individual oncological patients, as well as the objectives of repositioning of the existing medicinal products and search for molecular targets in the development of new targeted medicinal products.

The objectives are solved by the technology based on molecular profiling of pathological tissue samples, further analysis of molecular pathway activation profiles and calculation of Balanced Efficiency Score (BES).

The fresh tissue biosamples, FFPE tissue blocks or otherwise preserved tissue samples can serve as the pathological tissue samples. Preferably, the analysis is made for a pathological tissue of proliferative disease or oncological patient. Also, for the patient's pathological tissue, it is preferred to analyse sufficiently homogeneous area with proliferative phenotype. To this end, the tissue with proliferative phenotype can be additionally cleared or isolated from other surrounding tissues using the methods known to specialists.

The Oncobox platform is efficient for analysing a wide spectrum of large-scale molecular data: gene mutation profiles, mRNA expression data, microRNA expression data, quantitative proteomics data, and quantitative transcription factor binding sites data in gene regulatory regions.

The first addressable technical objective (1) is intracellular molecular pathway change analysis based on data types listed. Wherein, the measured intracellular pathways include signalling, DNA repair, metabolic, cytoskeleton rearrangement and other molecular pathways.

Wherein, the first technical objective is divided into several sub-objectives:

1.1. Development of molecular pathways database and assigning of pathway-based functions to the enclosed gene products 1.2. Development of algorithms for molecular pathway activation analysis for the experimental data on DNA mutations, mRNA, protein and microRNA expression, on profiles of transcription factor binding sites.

The second technical problem being solved (2) is personalized prediction of clinical efficiency of medicinal products for individual patients, including oncological patients.

The second technical objective is divided into the following sub-objectives:

2.1. Development of molecular targets database for targeted medicinal products.

2.2. Development of algorithms for personalized prediction of clinical efficiencies of medicinal products based on molecular pathway activation data and other molecular statistical data.

Oncobox Platform Organization Diagram.

The general operation principle of the Oncobox platform is shown in FIG. 1.

The Oncobox platform has a number of essential advantages compared to other published methods.

First, in contrast to other systems, it can simultaneously use an unparalleled wide range of multi-omics genetic data: information on gene mutations, profile of transcription factor binding sites, protein, mRNA and microRNA expression data. Wherein, the Oncobox platform introduces for the first time the methods of nominal prediction of the efficiency of targeted medicinal products with different specificities based on gene mutation profiles, microRNA expression data and transcription factors binding site profiles. Simultaneous use of different molecular data types provides a unique advantage to the Oncobox platform of choosing and validating the selection of the medicinal products using alternative methods. For the first time, the Oncobox platform enables uniform comparison of genomic, transcriptomic and epigenetic data available for an individual patient. Wherein, the final recommendation includes consensus drugs selected using the available types of data analysis to the most possible extent.

Second, as distinguished from other methods, the Oncobox platform uses a combination of molecular pathway activation level and special quantitative measure (relative expression or mutation burden) of genes—direct targets of drugs. This makes it possible to obtain the higher-quality ranking results for relative efficiencies of medicinal products as compared to the previously published methods, for example, application US20170193176A1, and article by Artemov et al., 2015. The comparison of data obtained using the Oncobox platform and some previously published approaches is given in Example 8.

Third, the Oncobox platform for the first time formalizes a requirement of data alignment (harmonization) during combination of the test sample gene expression profiles and the normal (control) sample gene expression profiles before the analysis and offers an innovative tool for its implementation.

Fourth, the Oncobox platform for the first time introduces an automatic annotation of molecular pathways. An innovative tool is offered to define a role of each gene product in each molecular pathway during the analysis of molecular pathway activation. This significantly reduces operational errors and increases the Oncobox performance by enabling analysis of any number of molecular pathways including any number of relevant gene products.

Another important distinction of the Oncobox system is an innovative method for calculation of Balanced Efficiency Score (BES) for each medicinal product. Based on this score, the drug efficiency estimation is made. BES is calculated using a single algorithm including summation of two basic members: Drug Efficiency Score MP, $DES_{MP}$ (reflects the contribution of molecular pathways) and Drug Efficiency Score TG, $DES_{TG}$ (reflects the contribution of individual molecular target genes), wherein, different weight coefficients for $DES_{MP}$ and $DES_{TG}$ varying from −1 to 1.5 are used for various medicinal products. Summation of DES members is introduced for the first time: $DES^{MP}$ and $DES^{TG}$, as well as division of the medicinal products into functional classes with the characteristic weight coefficients for $DES^{MP}$ and $DES^{TG}$ in the BES calculation formula. The medicinal products are classified into functional groups in accordance with their known mode of action and molecular specificity.

The offered method can be also used for repurposing of the existing medicinal products and for identification of new molecular targets during new medicinal product developments.

Intracellular Molecular Pathway Analysis

The quantitative molecular pathway analysis in the testing biosample is the first stage of the Oncobox system operation pipeline. To this end, the Oncobox system uses a single basic algorithm for molecular pathway analysis, for which the ability to minimize experimental measurement errors has been shown before (Aliper et al. 2017). For each of the analysed data types (DNA mutations, mRNA, protein and microRNA expression profiles, transcription factor binding profile), the Oncobox system uses specific modifications of the original algorithm.

The analysis is performed using the molecular pathway database with the automatically annotated functional roles of the individual gene products—participants of each pathway. For the Oncobox system, five types of functional roles are introduced for gene products: pathway activator, repressor, rather activator, rather repressor, and gene product with uncertain or inconsistent role.

Automatic annotation of functional roles of gene products from the molecular pathways database is one of the innovative features of the Oncobox platform. It is implemented as follows.

Algorithm for automatic annotation of functional roles and coefficients placement for the gene products for calculation of molecular pathway activation.

The algorithm was designed for assigning coefficient (activator/repressor role, ARR) to gene products to specify their roles in molecular pathway activation. This algorithm is based on the automatic analysis of protein-protein interaction graph for each particular pathway. This graph can be built manually or using any molecular pathway database, such as KEGG, biocarta, Reactome, etc. Genes are placed on the graph nodes, and the rib between two nodes symbolizes a protein-protein interaction between the corresponding gene products. Each rib of this graph is directed, as well as has a parameter indicating the protein-protein interaction: "activation" or "inhibition". For correct arrangement of ARR coefficients, this graph should be connected, wherein a weak connectivity is sufficient.

If the protein-protein interactions graph for a specific molecular pathway matches the above criteria, then ARR coefficients can be automatically assigned to the gene products included in this pathway. This is enabled by using the following recursive algorithm:

1) Initialization: the first (top) node is identified to be the central graph node. The two parameters N and M are then calculated for each node: N—number of nodes which can be reached when moving from the node V, M—number of nodes from which the node V can be reached. The central node will be such node V for which the N+M parameter is maximum. The value of ARR=1 is next assigned to the central top. From this top, ARR indexes are being recursively assigned to the other nodes.

2) Recursion R: for each node V, all nodes Pi to be found with the rib Pi→V or V→Pi in the graph. Each rib can be counted only once during recursion. Otherwise, the recursion can be endless in case of cyclic interactions occurring in the graph. If the rib has an "activation" parameter, temporary ARRtemp=1 is assigned to the node Pi. If the rib has an "inhibition" parameter, temporary ARRtemp=−1 is assigned to the node Pi. If the node Pi was never found previously in the graph traversal, ARR=ARRtemp would be assigned to the node Pi. If the node Pi was found previously in the graph traversal and the previously assigned ARR is equal to ARRtemp, then ARR=ARRtemp would be assigned to the node Pi. If the node Pi was found previously in the graph traversal and the previously assigned ARR is not equal to ARRtemp, then ARR would be assigned to the node Pi according to the conflict resolution rule. Conflict resolution rule: if a gene with already specified ARR is found in the graph traversal but according to the above rules, contradictory ARR values can be applied to this gene, then the conflicts should be resolved by the following rules: 1) if the signs of two ARR coefficients are different, the resulting ARR=0; 2) if ARRs are different by 0.5 and one of them is positive, the resulting ARR=0.5; 3) if ARRs are different by 0.5 and one of them is negative, the resulting ARR=−0.5. Then for each node Pi with the |ARR| module equal to 1, the recursion R is initiated.

3) As a result, the algorithm will assign ARR to the graph nodes. These coefficients can be used to calculate the molecular pathway activation strengths according to the above formula.

Therefore, the gene products included in the molecular pathways database will have the assigned ARR values representing their functional significances in the given molecular pathway.

For generation of the molecular pathway database, both the published and the user-defined molecular pathway catalogues can be used. The published catalogues include collections of data, such as BioCarta, KEGG, NCI, Reactome and Pathway Central (Buzdin et al., 2017). They collect information about 3,125 molecular pathways which collectively cover about 11,000 protein-coding human genes. To be used in the Oncobox system, each molecular pathway database should include the following information:

1) Unique identifiers for all genes whose products are included in the curated molecular pathways, 2) Role of each relevant gene product in every curated molecular pathway: role of activator, repressor, neutral role, or roles of interim activator or repressor.

The basic algorithm for molecular pathway activation analysis is based on the acceptance of the following major principles.

First, the molecular interaction graph in each pathway is supposed in the form of two parallel chains of events, one leading to activation and another—to inhibition of a molecular pathway.

Second, expressions of all the gene products participating in a pathway with "activator" roles are supposed to be lower when the pathway is inhibited, and vice versa. This principle is based on the published data that the deeply unsaturated states of each of the proteins-signal transducers in an individual molecular pathway are congruent with the low pathway activity states (Kuzmina and Borisov 2011; Aliper et al. 2017).

This is important to note that although the basic algorithm includes a notion of gene "expression" (i.e. this means mRNA and protein relative contents in normal interpretation), other measured molecular characteristics can come down to it:

microRNA expression (affecting target gene expression via specific inhibition of target mRNAs), transcription factor binding (regulating gene expression at the transcription level), mutations in genomic DNA (affecting wild type gene expression via mutant allele occurrence). The authors use the term "reduced gene expression" covering the gene expression calculation according to the above molecular data types.

The Oncobox system assumes all gene products participating in a molecular pathway as those having potentially equal possibilities to cause activation or inhibition of this pathway. For calculating molecular pathway activation levels, the Oncobox system utilizes the following basic formula:

$$PAL_p = \Sum_n NII_{np} \cdot ARR_{np} \cdot \ln CNR_n / \Sum_n |ARR_n|,$$

where $PAL_p$—molecular pathway p activation level; $CNR_n$ (case-to-normal ratio)—ratio of the protein-encoding gene n product concentrations in the test sample and in the norms (average value in the control group); ln—natural logarithm; $NII_{np}$—index of gene product n assignment to the pathway p, assuming the values equal to one for gene products included in the pathway and equal to zero for gene products not included in the pathway; discrete value $ARR_{np}$ (activator/repressor role) is deposited into the molecular pathway base and determined for a gene n in the pathway p as follows:

$$ARR_{np} = \begin{cases} -1; \text{ protein and - signal repressor in pathway } p \\ -0.5; \text{ protein } n - \text{ rather signal repressor in pathway } p \\ 0; \text{ unclear repressor or activator role in pathway } p \\ 0.5; \text{ protein } n - \text{ rather signal activator in pathway } p \\ 1; \text{ protein } n - \text{ signal activator in pathway } p \end{cases}$$

The major distinguishing feature of the basic algorithm differing it from the previously published methods (see, for example, Buzdin et al., Front Genet 2014) is that in the Oncobox system the molecular pathway activation strength is normalized on the number of genes-participants of a molecular pathway with the known functional roles, represented by the $|ARR_n|$ parameter.

Depending on the available type of molecular data for a biosample under investigation, the ln $CNR_n$ parameter is calculated in different ways as a part of the basic algorithm, i.e. this is the logarithm of the ratio of the gene expression n in the test sample and in the control sample. Below are the options for the ln CNRn calculation depending on the different types of molecular data available.

(1)—ln $CNR_n$ for Genomic DNA Mutations Data.

In each sample, the MR (mutation rate) is calculated for every gene included in a molecular pathway p:

$$MR_n = 1000 \Sum N_{mut(n)} / L_{cds(n)},$$

where $N_{mut(n)}$—number of detected mutations in the protein-coding part of gene n in the test sample; $L_{cds(n)}$—length of the protein-coding part of gene n in the base pairs.

In turn, ln $CNR_n$ is calculated according to the following formula:

$$\ln CNR_n = \ln CNR(MR_n),$$

where $CNR(MR_n)$—ratio of MR in the test sample to the average MR in the control group for gene n.

(2)—ln $CNR_n$ for Transcription Factor Binding Site Data.

In this application, a consensus transcription starting point is determined for each gene. For each transcription starting point, the neighbourhood that is the region from 5 kbp above the transcription starting point to 5 kbp below the transcription starting point is determined for every relevant gene. In this neighbourhood, the number of mapped transcription factor binding sites is calculated. Then GRES (Gene Record Enrichment Score) is calculated for every gene:

$$GRES_n = m \cdot TES_n / \Sum_{i=1}^{m} TES_i,$$

where $GRES_n$—GRES value for gene n; m—total number of relevant genes for a given testing sample; $TES_n$—number of mapped transcription factor binding sites in the neighbourhood of gene n; i—index corresponding to gene identifier; $TES_i$ sum by gene number m—total number of mapped transcription factor binding sites in the neighbourhood of all test genes. For each gene, GRES values allows to rank the saturation level of the transcription factor binding sites. For example, GRES=1 means average saturation level among all genes; GRES>1 means saturation level that is higher than the average for all genes; GRES<1, to the contrary, means that the gene is depleted in transcription factor binding sites than the average for all genes.

Finally, ln CNRn is calculated according to the following formula:

$$\ln CNRn = \ln CNR(GRES_n),$$

where $CNR(GRES_n)$—ration of GRES in the test sample to the average GRES in the control group for gene n.

(3)—ln $CNR_n$ for mRNA Expression Data.

One of the distinguishing features of the Oncobox system is that the original method of common normalization is applied to the test samples along with the groups of relevant normal samples for mRNA profiles before the molecular pathway activation calculations.

The information containing in the publicly available gene expression profile databases includes data obtained using different experimental platforms and reagents, including microarray hybridization and deep sequencing. Such databases contain the results for more than 2 million samples obtained in more than 70 000 experiments (Cancer Genome Atlas Research Network 2008; https://www.ncbi.nlm.nih.gov/geo/).

The results of quantitative gene expression profiling done using different experimental platforms and in different series of experiments are as a rule hardly comparable (Demetrashvili et al. 2010). To reach the satisfactory data homogeneity level for the compared expression profiles, the Oncobox system applies an innovative method for gene expression profile harmonization Shambhala that is suitable for standardization of the results received both using single and different experimental platforms.

The following previous widely used harmonization methods can be mentioned here: DWD (distance-weighted discrimination) (Huang et al. 2012), XPN (cross-platform normalization) (Shabalin et al. 2008) and PLIDA (platform-independent latent Dirichlet allocation) (Deshwar and Morris 2014), they embody deep restructuring of gene expression profiles. However, those methods can use only the data generated by maximum two experimental platforms, or can they merge maximum two gene expression datasets. As a rule, these harmonizer methods are based on identification of gene or protein clusters which are similarly expressed in both datasets, and then a stepwise approximation of the expression profiles received on two different experimental platforms is made within one cluster. the inability to harmonize more than two sets of expression data is a serious but not a single drawback of the current methods. The number of gene expression profiles in each of the datasets under comparison as a rule is limited by a maximum threshold value of one hundred samples. This prevents using this group of methods for high throughput multiple analyses of gene expression data including hundreds and thousands of samples in every experimental dataset.

To solve this problem, the Oncobox system utilizes the innovative original Shambhala method developed the Oncobox authors team to ensure high quality harmonization of the gene expression profiles obtained using various platforms and to bring them in a universal comparable form. The Shambhala method enables harmonization of any number of samples under comparison obtained using any number of experimental platforms.

Figure 2:
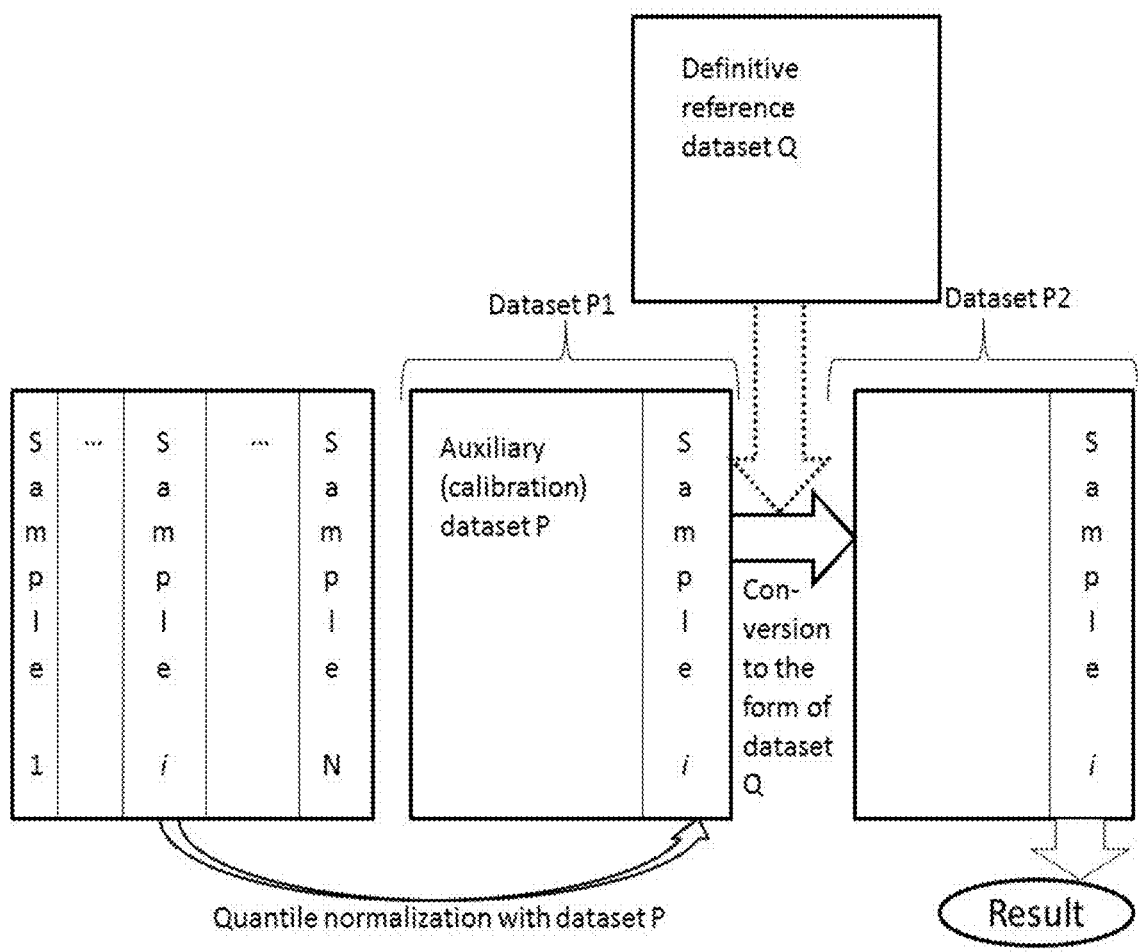
FIG. 2. Diagram of Shambhala algorithm for universal harmonization of expression profiles. Various gene expression samples (profiles) (1, . . . , N) (see the left bottom box) are added one by one to auxiliary (calibration) set of profiles P with the use of quantile normalization (Bolstad et al. 2003). Then the resulting set of expression profiles P1 is converted into a definitive form that is characteristic for a set of standard expression profiles Q with the use of piecewise harmonization (Shabalin et al. 2008). The distinctive feature of this conversion as compared to other published approaches is that (1) during conversion, only a set of profiles P1 is subject to iterative changes while the set Q remains constant; (2) for gene and sample clustering in the sets of profiles P1 and Q, a spherical (cosine) but not a barycentric, as in XPN (Shabalin et al. 2008), proximity measure is used. Upon completion of these procedures, the sample/profile i=(1, . . . , N) is considered harmonized.

Shambhala uses gene and image clustering by means of stochastic genetic algorithms, as well as piecewise linear iterative approximation of gene expression profiles. Shambhala algorithm includes the following distinguishing features (FIG. 2):

1. Bringing (conversion) of the harmonized set of profiles (P1) to the form of expression values distribution that is similar to the reference (specific) set of the expression profiles (termed Q-set). A set of one hundred expression profiles extracted from the Genotype Tissue Expression (GTEx) dataset (GTEx Consortium 2013) is used as a reference (specific) dataset of the expression profiles. The GTEx dataset (GSE45878) was obtained using mRNA hybridization on Affymetrix Human Gene 1.1 ST (GPL16977) microarrays of. During data conversion, P1 dataset is iteratively approximates while Q-dataset remains constant. This conversion results in a set of expression profiles P2 representing a set of transformed profiles from P1-set, that are similar to a shape characteristic for the reference (specific) set of profiles Q.
2. To ensure better stability (lower noise due to stochastic algorithm of gene clustering included into the iterative harmonization algorithm), a cosine metrics of set proximity is used instead of that used in the other methods, for example, instead of Euclidean barycentric (Krishna, 1999; Hornik, 2012) that is used in XPN (Shabalin et al. 2008).
3. To ensure stable conversion into the form of the reference dataset Q, each of the converted profiles (i=1, . . . N), taken one by one, is subjected to conversion as the part of the above dataset P1. To generate P1, each of the expression profiles i (i=1, . . . N) is initially quantile normalized (Bolstad et al. 2003b) with the specified carrier (auxiliary) set of profiles (P) ensuring uniform calibration scale of the expression values before conversion into the form of dataset Q. Finally, the dataset P2 resulting from this conversion will comprise a harmonized gene expression profile i (i=1, . . . N), see FIG. 2.

Following Shambhala harmonization, direct analysis of gene expression levels is performed. The molecular pathway activation is calculated according to the above main PAL calculation formula, where ln CNR is natural logarithm of the ratio of harmonized gene n expression values in the test sample to the norm (average value for the control group).

(4)—ln $CNR_n$ for Quantitative Proteomic Data.

To analyse the molecular pathway activation at the level of protein expression, the Oncobox system uses the Shambhala method at the first stage for harmonization of testing profiles with thegroups of normal samples similarly as for the previous application.

The molecular pathway activation is then calculated, where a natural logarithm of the ratio of harmonized protein expression level n in the test sample to the norm (average value for the control group) is taken as ln CNR.

(5)—ln $CNR_n$ for microRNA Data.

This method of data analysis is based on the use of gene a database of gene products—molecular targets of individual microRNAs. To be included in the Oncobox system, microRNA targets database must contain the following information:

1) microRNA unique name and/or identifier,
2) list of unique identifiers for gene products—molecular targets of this microRNA.

In the Oncobox system, the microRNA effect on the adjusted gene expression level is calculated based on the assumption that microRNA molecules functionally inhibit their mRNA targets. The increased microRNA level, therefore, leads to decreased adjusted expression levels of the relevant target mRNAs, and vice versa. Wherein, each gene product may have several regulatory microRNAs, and each microRNA may have several gene targets.

Wherein, ln $CNR_n$ is defined according to the following formula:

$$\ln CNR_n = -\Sigma_i \ln miCNR_i \cdot miII_{i,n},$$

where n—gene product being analysed, j—the total number of microRNAs under investigation, i—individual microRNA being analysed. Boolean variable of microRNA involvement index ($miII_{i,n}$) indicates if the gene product n is a molecular target for microRNA i. Wherein, $miII_{i,n}$ assumes a value that is equal to 1 when the analysed gene product n is a molecular target for microRNA i and a value that is equal to 0 when is not. $miCNR_i$ is a ratio of the established microRNA i expression levels in the test sample to such the average value for the control group. The negative coefficient before the summation symbol reflects the inhibiting role of a microRNA for the corresponding target gene product.

To ensure optimal ranking of clinical efficiencies of the targeted medicinal products, the combination of Oncobox analyses using various types of molecular data received from the patient's pathological tissue is preferred. One of the possible approaches is combining the analyses based on protein expression data with the analysis based on pathological tissue-driven mutations data. These two types of analyses can functionally complement each other and are preferred for embodiment of defining the clinical efficiencies of the targeted medicinal products, provided that the initial molecular data are of a sufficient quality. Other data types (transcription factor binding, microRNA and mRNA expression) mainly affect the protein expression levels in the molecular pathways, as well as expression levels of the target proteins themselves, and act indirectly. These data types can be used in the embodiment of defining the clinical efficiencies of the targeted medicinal products in cases when the protein expression data are unavailable or of insufficient quality.

To receive information from control samples of a healthy subject, the published data publicly available for certain tissue (for example, mRNA expression data), or preferably experimental data received from control samples of healthy subjects on the same equipment as the data from the patient's test sample can be used. In the latter case, they can be received simultaneously with the analysis of pathological tissue samples of a certain patient. To improve accuracy of estimation during the control sample selection, it is recommended to use healthy subject samples having as similar physiological characteristics with the patient as possible, for example, gender and age. The minimum condition is the use of one control sample for one patient's sample. To improve the accuracy of estimation, it is advised to use three—twenty control samples that makes it possible to efficiently eliminate possible deviations existing in the individual control data. Averaging means the use of arithmetic mean of the averaged values. In some embodiments of the current invention, geometric mean of the averaged values is used.

In preferred embodiments, the genome-wide data are to be received from the patient's sample and control sample. But the embodiment is possible with lesser data coverage. The data evaluating the specified parameters (microRNA, protein or mRNA expression levels, transcription factor binding profile) for at least 80% of all gene products included into the selected molecular pathways listed in the respective Oncobox pathway database, can be taken as relevant. Wherein, it is strongly recommended to obtain data for all gene products being known molecular targets of the testing drugs. The minimum required set of quantified gene products depends on (i) the quantity and composition of testing panel of drugs and (ii) the list of molecular pathways accepted as the reference database by the Oncobox user.

For each targeted medicinal product, the data are obtained from at least one control tissue sample without proliferative/oncological phenotype, wherein the control sample is taken from the tissue of the same tissue type as the specified patient's biosample. Tissue sample without proliferative/oncological phenotype means a tissue sample taken either from a "healthy" subject without the same oncology disease as the patient examined has, or from the patient examined but from the area not affected by the oncological disease.

For embodiment, genome suboptimal quality data can be used. For example, any types of incoming expression data ensuring uniform determination of the expression strength of each gene product to be analysed as well as detection of at least 1000-fold differences in the expression levels between separate gene products can be used for mRNA and microRNA expression data. Any type of incoming genome and/or exome sequencing data fully covering protein coding regions of genes under study can be used for assessments of genomic DNA mutation profiles, with 100-fold minimum average level of coverage. For transcription factor binding data, numbers of analysed mapped binding sites should be not less than 10-fold gene number to be analysed.

Calculation of the Balanced Efficiency Score (BES) for Target Anti-Cancer Medicinal Products Medicinal products (drugs) are products with known molecular targets. In the description of this invention, the term "target product" is limited by medicinal products of certain 16 classes or types, given in Table 1. These classes cover the main currently known target drugs used in clinical practice. Medicinal products under numbers 8, 9, 10, 14, 15 in Table 1 are immunoglobulin-based (antibody-based) drugs while the drugs of other types in Table 1 are low-molecular weight chemical compounds (small molecules).

The information of the drug manufacturers, as well as scientific publications in specialized pharmacological, biochemical and biomedical journals can be used as the sources to create molecular targets database for each targeted medicinal product. To be used in the Oncobox system, database for each included drug should include the following information:

1. drug unique name and/or identifier,
2. list of unique identifiers for gene products—molecular targets for this drug,
3. drug type by the mode of action (according to Table 1).

The Oncobox system is capable of modelling the drug ability to block pathological changes in molecular pathways and simultaneously block gene products with pathological increase in the expression level. In contrast to other known analogues, the Oncobox platform uses the innovative parameter of Balanced Efficiency Score (BES) for each drug as a target drug efficiency measure. Wherein, the data on molecular pathway activity in a test sample and the data on expression levels of gene products—targets of a certain drug are simultaneously used for the BES calculation. BES value is calculated according to the formula:

$$BES_d = a \cdot DES^{MP}_d + b \cdot DES^{TG}_d,$$

where d—target drug under investigation; a and b—weight coefficients varying from −1 to 1.5 depending on the target drug type d; $DES^{MP}_d$ (Drug Efficiency Score for Molecular Pathways)—drug efficiency index d calculated based on activity levels for molecular pathways containing molecular targets of drug d; $DES^{TG}_d$ (Drug Efficiency Score for Target Genes)—drug efficiency index d calculated based on levels of expression of individual gene products—molecular targets of drugs.

To calculate $DES^{MP}$, the following formula is used:

$$DES^{MP}_d = \Sigma_t DTI_{d,t} \cdot \Sigma_p PAL_p \cdot AMCF_p \cdot NII_{t,p},$$

where d—unique identifier of target drug; t—unique identifier of gene product-target of drug d; p—unique identifier of signalling pathway; $PAL_p$—molecular pathway p activation strength; discrete value AMCF (activation-to-mitosis conversion factor) to be determined as follows:

AMCF=1, when the activation of a pathway facilitates cell survival, growth and division;

AMCF=0, when there are no data whether the molecular pathway activation facilitates cell survival, growth and division, or when such data available for researcher are conflicting;

AMCF=−1, when the activation of a pathway prevents cell survival, growth and division.

Discrete value DTI (drug-target index) is defined as follows:

$$DTI_{dt} = \begin{cases} 0, & \text{when drug } d \text{ doesn't affect gene product } t \\ 1, & \text{when drug } d \text{ affects gene product } t \end{cases}$$

Discrete value NII (node involvement index) is defined as follows:

$$NII_{tp} = \begin{cases} 0, & \text{there is no gene product } t \text{ in pathway } p \\ 1, & \text{there is gene product } t \text{ in pathway } p \end{cases}$$

To calculate $DES^{TG}$, the following formula is used:

$$DES^{TG}_d = \Sigma_t DTI_{d,t} \Sigma_p \ln CNR_t \cdot ARR_{t,p} \cdot AMCF_p \cdot NII_{t,p},$$

where d—unique identifier of target drug; t—unique identifier of gene product—molecular target of drug d; p—unique identifier of signalling pathway; $CNR_n$ (case-to-normal ratio)—ratio of the expression levels of protein-coding gene t in the test sample to the norm (averaged expression level for a control group); ln—natural logarithm; definitions of $DTI_{d,t}$, $AMCF_P$ and NII are similar to those given above; discrete value $ARR_{t,p}$ (activator/repressor role) is defined for a gene product t in the pathway p as follows and deposited into the molecular pathway database:

$$ARR_{np} = \begin{cases} -1; & \text{gene product } n \text{ is repressor of pathway } p \\ -0.5; & \text{gene product } n \text{ is rather repressor of pathway } p \\ 0; & \text{activator/repressor role of gene product } n \text{ in pathway } p \text{ is unclear or unknown} \\ 0.5; & \text{gene product } n \text{ is rather activator of pathway } p \\ 1; & \text{gene product } n \text{ is activator of pathway } p \end{cases}$$

To calculate the Balanced Efficiency Score (BES) for drug d, weight coefficients a and b are used, which differ depending on the drug type. Values of the coefficients are given in Table 1.

For low-molecular tyrosine kinase inhibitors (nibs), both weight coefficients are equal to 0.5 representing equal significance of target molecular pathway activation and target gene expression levels in the pathological tissue sample tested. This is related to nibs capability of blocking their molecular targets and thus inhibiting their activities, as well as modulating the cell signalling via related molecular pathways. For hormones, both weight coefficients are equal to −0.5, due to the fact that they activate but not inhibit their molecular targets and act accordingly also on their target molecular pathways. For antihormones, coefficients are equal to 0.5 again which is due to their inhibition effect on their molecular targets, hormone products and on the respective molecular pathways. For retinoids, both coefficients are equal to 0.5 because these drugs bind retinoic acid receptors and activate a number of dependent molecular pathways. For rapalogs (rapamycin analogs), both coefficients are equal to 0.5 because they demonstrate their inhibition effect by directly binding with their molecular targets, and act accordingly on the relevant molecular pathways. For mibs (proteasome inhibitors), both coefficients are equal to 0.5 because these drugs demonstrate the inhibition effect when binding with their molecular targets, and act accordingly on the relevant molecular pathways and proteasome signalling. For VEGF blocking agents, a=0 and b=1 because these drugs directly blocks the VEGF molecules in the blood flow while not binding with the molecular targets inside the cell or on the cell surface and, therefore, don't directly affect the intracellular signalling. For monoclonal antibodies that bind with their molecular targets on the cell surface (mabs), a=0 and b=1 as their main mode of action consists in activation of immune cytotoxical response against the cells having bound mab molecules on their surface and does n't deal with strong modulation of signalling by affecting molecular pathways. Killermabs consist of antibodies against molecular targets on the cell surface, chemically bound with cytotoxic agents. When binding with their targets on the cell surface, the killermabs kill these cells, thus demonstrating therapeutic mechanism not related to intracellular molecular pathway activation. For them, a=0 and b=1.5; in this case the increased coefficient b represents proprietary high cytotoxical activities of these drugs. For drugs blocking de novo tubulin polymerization, a=0 and b=1; this represents the indefinite function of many targeted pathways for these drugs in cell survival and proliferation, as well as their direct inhibitory effect on their molecular targets. The same coefficients are also set for histone deacetylase inhibitors due to the same reasons concerning their mechanism of action. For DNA-alkylating agents, a=0 и b=−1 reflecting the indefinite functions of the majority of targeted pathways for cell survival and proliferation, as well as direct inhibitory effect on these drugson of DNA repair proteins that target the alkylated DNA (reflected by the coefficient b=−1). For immunotherapeutic drugs, both coefficients are equal to 0.5 due to dependence of their effect on the availability of both direct molecular targets and molecular pathway activation profiles related to tumour infiltration with lymphocytes. Similarly, the poly-ADP ribose polymerase blocking drugs inhibit DNA repair and depend on both availability of direct molecular targets and on the activities of targeted molecular pathways. This is reflected by both coefficients a and b equal to 0.5.

TABLE 1

Values of weight coefficients a and b for 16 classes of target anti-cancer medicinal products.

| No | Type | a and b values | Drug description |
|---|---|---|---|
| 1 | Nibs | a = 0.5<br>b = 0.5 | Low-molecular weight tyrosine kinase inhibitors |
| 2 | Nibs* | a = 0.5<br>b = 0.5 | Nibs being active only in case of diagnostic mutations |
| 3 | Hormones | a = −0.5<br>b = −0.5 | Binding with hormone receptors |
| 4 | Anti-hormones | a = 0.5<br>b = 0.5 | Reducing the level of hormone production or sensitivity to hormones |
| 5 | Retinoids | a = 0.5<br>b = 0.5 | Binding with retinoic acid receptors |

TABLE 1-continued

Values of weight coefficients a and b for 16 classes of target anti-cancer medicinal products.

| No | Type | a and b values | Drug description |
|---|---|---|---|
| 6 | Rapalogs | a = 0.5<br>b = 0.5 | Rapamycin analogues; blocking the MTOR signalling |
| 7 | Mibs | a = 0.5<br>b = 0.5 | Proteasome blocking agents |
| 8 | VEGF blocking agents | a = 0<br>b = 1 | Antibodies neutralising VEGF molecules in the blood flow |
| 9 | Mabs | a = 0<br>b = 1 | Monoclonal antibodies binding with proteins on cell surface |
| 10 | Killermabs | a = 0<br>b = 1.5 | Antibodies covalently linked to small molecules (toxins), killing cells when directly binding with them |
| 11 | Tubulin blocking agents | a = 0<br>b = 1 | Blocking the microtubule homeostasis in proliferating cells |
| 12 | HDAC inhibitors | a = 0<br>b = 1 | Inhibiting histone deacetylases |
| 13 | Alkylating agents | a = 0<br>b = −1 | Alkylating DNA in proliferating cells |
| 14 | Immunotherapeutic drugs, type 1 | a = 0.5<br>b = 0.5 | Monoclonal antibodies blocking immunosuppression by binding with T-cell surface receptors |
| 15 | Immunotherapeutic drugs, type 2 | a = 0.5<br>b = 0.5 | Monoclonal antibodies blocking immunosuppression by binding with T-cell receptor ligands |
| 16 | PARP blocking agents | a = 0.5<br>b = 0.5 | Inhibiting poly-ADP ribose polymerase and blocking DNA repair |

The Oncobox system makes it possible to rank the efficiencies of anti-cancer medicinal products which belong to 16 different classes (Table 1). Classification of the medicinal product is made according to their known modes of action and molecular specificities. Then the Balanced Efficiency Score (BES) is calculated in different ways for different classes of anti-cancer drugs (Table 1). Then, according to BES values, a personalized rating of target anti-cancer medicinal products for the test biosample, for example, taken from the oncological patient, is built, wherein the medicinal products with a positive BES value (BES>0) can be recommended.

Thus, the present invention provides a method of predicting clinical efficiencies of targeted medicinal products for treatment of proliferative disease or oncological patients selected from the targeted medicinal product groups that includes at least the following stages: (a) receiving information about molecular targets for each targeted medicinal product selected from the group specified; (b) receiving the patient tissue sample with proliferative/oncological phenotype; (c) receiving data of at least one type for the specified sample, and the data type can be the following: (i) total mRNA expression data, (ii) high throughput protein expression data, (iii) high throughput transcription factor binding site data, (iv) high throughput mutations data within genomic DNA, (v) high throughput microRNA expression data; (d) receiving data from at least one control tissue sample without proliferative phenotype, wherein the control sample is taken from the tissue of the same type as the specified patient's tissue, and the control sample data type matches the data type received at stage (c); (e) receiving of at least one type data on molecular targets for each targeted medicinal product from the specified sample, and the data type is selected from the following list: (i) molecular target mRNA expression data, (ii) molecular target expression data, (iii) molecular target gene mutations data, (iv) transcription factor binding site data for molecular target genes, (v) microRNA expression data affecting the molecular target gene expression, wherein each of the data type (i)-(v) received at stage (e) matches the data type, respectively (i)-(v), received at stage (c); (f) receiving molecular target data for each targeted medicinal product from at least one control tissue sample without proliferative phenotype, wherein the control sample is taken from the tissue of the same type as the specified patient's tissue; the control sample data type matches the data type received at stage (e); (g) defining the quantitative indicators of the product efficiency for each data type (i)-(v) using data received at stages (c)-(f); (h) defining the clinical efficiency for each targeted medicinal product from the targeted medicinal products group using the average efficiency quantitative indicators defined at stage (g).

The Balanced Efficiency Score (BES) for each data type (i)-(v) is calculated by summing up two parts ($DES^{MP}_d$ and $DES^{TG}_d$) to be calculated based on molecular pathway activity data for the test sample and reduced gene product—molecular targets expression data d), considering the weight coefficients (a and b) which depend on the drug type and are disclosed in Table 1. For calculation of both parts ($DES^{MP}_d$ and $DES^{TG}_d$), the data received from the patient's sample are normalized to the relevant data of the same type received from at least one control sample.

In the preferred embodiment, the medicinal product efficiency score d for each data type (i)-(v) is calculated using the following formula:

$$BES_d = a \cdot (\Sigma_t DTI_{d,t} \cdot \Sigma_p PAL_p \cdot AMCF_p \cdot NII_{t,p}) + b \cdot (\Sigma_t DTI_{d,t} \cdot \Sigma_p \ln CNR_t \cdot ARR_{t,p} \cdot AMCF_p \cdot NII_{t,p}).$$

If there are several available types of the patients data, then quantitative indicators are calculated independently for each data type (i)-(v), and then the average efficiency score is used to define the clinical efficiencies of the targeted medicinal products.

The method of defining the clinical efficiencies of the targeted medicinal products can be embodied with the use of computing device comprising the following components:

one or more processing units, one storage memory at least, and, preferably, input/output interfaces, networking means and other components. The processing unit of the device performs main calculation operations required for modules functioning of the command running device. The processing unit runs necessary machine-readable commands comprised in the RAM. Storage memory means any information storage capable of storing necessary program logic to provide for the required functionality. The data storage memory means can be in the form of HDD, SSD disks, RAID, flash-memory, optical drives (CD, DVD, MD, Blue-Ray), and so on. Selection of interfaces depends on certain version of the computing device that can be a PC, mainframe, server cluster, thin-client, smart-phone, cash register, and so on. The following can be used as input/output means: keyboard, joystick, display (touch display), projector, touchpad, mouse, trackball, lightpen, speakers, microphone, and so on.

The Oncobox applications for molecular pathway activation strength analysis, drug efficiency ranking, discovery of new biomarkers and molecular targets for new drugs, repurposing of medicinal products are illustrated with the examples below.

The examples of the system operation are given below to disclose the characteristics of this invention and they should not be considered as confining the scope of the invention in any way.

Figure 3:
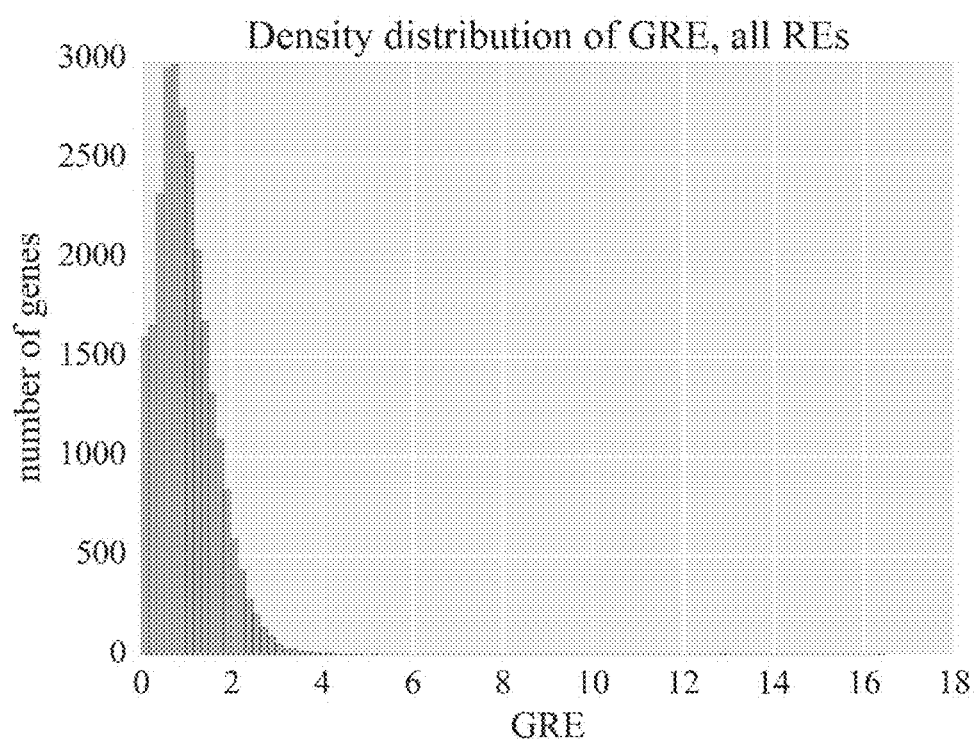
FIG. 3. Distribution of human protein encoding genes by GRES values (shown as GRE on the diagram).

Example 1. Calculation of the Molecular Pathway Activation Index Based on Epigenetic Marker Concentration Data Genome-wide binding profiles for 225 proteins-human transcription factors (TFs) received by different laboratories in chromatin immunoprecipitation experiments (ChIP-seq) for cell line K562 (erythroleukemia, immortalized cell line) were uploaded from the ENCODE database (https://www.encodeproject.orq/chip-seq/transcription factor/). The profiles represented a control-normalized—TF binding intensities in bedGraph format (https://genome.ucsc.edu/goldenpath/help/bedgraph.html). In accordance with the ChIP-seq data processing protocol, the human genome hg19 reference assembly was staged by the Burrows-Wheeler algorithm using BWA program (https://www.encodeproject.org/pipelines/ENCPL220NBH/). fastq-file merge with raw data, alignment to reference genome and filtration were made with BWA, Samtools, Picard, Bedtools and Phantompeakqualtools (https://www.encodeproject.org). Profiles of the control-normalized TF binding intensities were obtained from Macs (https://www.encodeproject.org/pipelines/ENCPL138KID/). These profiles were mapped in the 5 thousand base pairs neighborhood relative to consensus transcriptional start sitefor protein-coding human genes using USCS Browser, https://genome.ucsc.edu/cgi-bin/hgs, Table RefGenes). GRES (FIG. 3) and $CNR_{(GRES)}$ were calculated for each gene, and then PAL—for each molecular pathway.

Therefore, the Oncobox system was able to identify the groups of genes and molecular pathways activated in the tumour cell line K562. The strongest upregulated processes were characterized, such as: protein synthesis, DNA replication and repair, nucleus and chromatin structure maintenance, vesicular transport and cytoskeleton. In both cases, activation of innate immune system pathways was found out that is characteristic for myeloid cell line.

Figure 4:
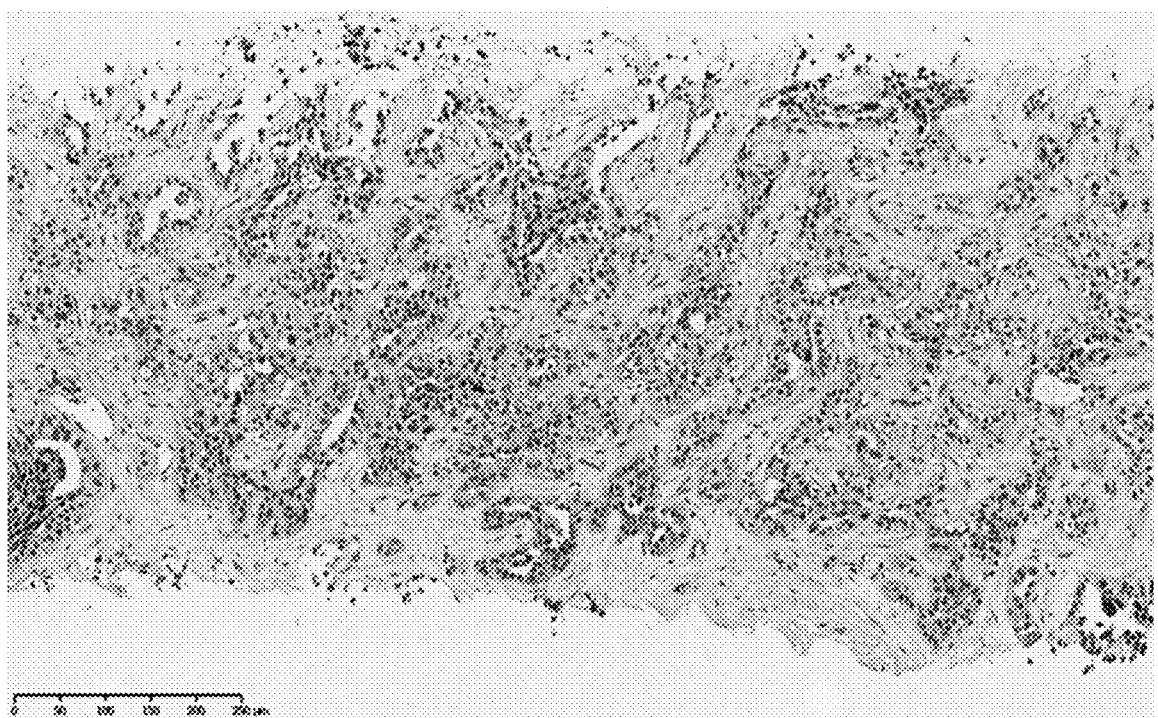
FIG. 4. Haematoxylin and eosin staining indicates moderately differentiated intrahepatic cholangiocarcinoma.

Example 2. Calculation of Oncological Medicinal Product Activity Rating for Individual Tumour Based on Molecular Pathway Activities According to mRNA Expression Data The rating of potentially efficient anti-cancer target drugs for a 72-years old patient with histologically distinctive moderately differentiated intrahepatic cholangiocarcinoma (FIG. 4). The patient was diagnosed in October 2015 with the following symptoms: moderate body weight loss, pain in right hypochondrium, loss of appetite and asthenia, with 70% Karnovsky index. The magnetic resonance imaging (MRI) proved the diagnosis during diagnostics. The tumour was not surgically excised due to advanced stage, several intrahepatic masses and lung metastasis.

At first, the patient received treatment that was considered the best clinical practice: four courses of chemotherapy (2 courses of gemcitabine combined with capecitabine and next 2 courses of gemcitabine combined with cisplatin) were conducted till May 2016. The treatment was ineffective, and the tumour increased according to MRI; additional metastatic tumours appeared in left and right lobes which spread to bile duct and gall bladder. Karnovsky index decreased by 60%. The patient did not respond to treatment, and the extended molecular analysis of tumour was performed using Oncobox system to identify alternative treatment options.

At first, total RNA was isolated from tumour sample and used to measure expression levels for 2,163 genes with CustomArray Inc. (USA) equipment using the microarray hybridization method. These 2,163 genes participate in major human signalling pathways associated with cancer, and also act as the molecular targets of anti-cancer medicinal products. Liver samples without pathological characteristics were taken from healthy donors and used as normal tissue controls. Using the Oncobox algorithm, the rating of target drugs was formed according to the BES values obtained (Table 2).

Table 2. Rating of the most efficient medicinal products for the patient with cholangiocarcinoma according to Oncobox test results.

In according with the Oncobox test results, in May 2016 the patient received target tyrosine kinase inhibitor drug Sorafenib. In October 2016, MRI detected tumour moderate development that corresponds to stable disease according to RECIST classification. Furthermore, after treatment with Sorafenib, there was detected pain elimination in right hypochondrium. MRI dated January 2017 detected progressing tumour and additional nodes in the right lung. Therefore, the period till progression made about 6 months. In addition, the following adverse effects appeared: reddening, edema, pains in palms of the hands and bottoms of the feet. It was a doctor decision to change treatment the medicinal product Pazopanib, another tyrosine kinase inhibitor recommended according to the Oncobox test. Treatment with Pazopanib started in January 2017. The check MRI in June 2017 showed moderate tumour development. Wherein, change in treatment has managed adverse effects of Sorafenib and generally improved the quality of life of the patient. As of October 2017, the patient was alive and physically active, with the Karnovsky index of ~100%.

This clinical case evidences that the personalized prescription of tyrosine kinase inhibitor with the Oncobox system can be efficient from the point of view of general survival and quality of life of the patients with metastatic cholangiocarcinoma.

Example 3. Rating of Oncology Medicinal Products for Colorectal Cancer Based on Genomic DNA Mutation Data The rating of the most relevant target drugs was generated for 105 medicinal products based on genome-wide data of 1,441 cases of colorectal cancer using the Oncobox platform. Data were extracted from database COSMIC v76 (The Catalogue of Somatic Mutations In Cancer) (Forbes et al. 2008) and contained information about 1,165,882 mutations in 19,897 genes.

The top positions of the rating are shown on Table 3 (nine medicinal products with maximum Balanced Efficiency Score (BES)).

Table 3. List of medicinal products having the top positions in the rating of potential effective drugs based on MDS.

Example 4. Modelling of New Molecular Targets for Anti-Cancer Medicinal Products Using DNA Mutations Data To estimate the mutation profile of the primary malignant liver tumours, the genome-wide sequencing data from database COSMIC v76 were used (The Catalogue of Somatic Mutations In Cancer) (Forbes et al. 2008), comprising records about 852,964 mutations in 19,491 genes of 1,654 tumour samples. The normalized mutation rates (NMR) were determined for all genes. Then, the molecular pathway data received from the largest publicly available databases were integrated into a single database: Reactome [doi: 10.1093/nar/gkt1102], NCI Pathway Interaction Database [doi: 10.1093/nar/gkn653], Kyoto Encyclopedia of Genes and Genomes [doi: 10.1093/nar/gks1239] и HumanCyc [(www.humancyc.org)]. For the purpose of statistical analysis sufficiency, only the molecular pathways comprising more than 10 genes were selected for further analysis, thus forming 1,753 pathways comprising 8,755 genes. PAL values were calculated for all molecular pathways. 8,755 virtual medicinal products, each having one gene product from the pathway database as a target, were then rated as a spectrum of potential target products. For all gene products—potential targets, Balanced Efficiency Scores were defined using the Oncobox platform.

As a result, the potential gene targets were identified for new therapeutic agents development. The following potential gene targets can serve as examples (Table 4).

Table 4. Ratings by Balanced Efficiency Score for genes—potential therapy targets calculated for malignant liver tumours using the Oncobox system.

Example 5. Repurposing of Known Medicinal Products for Malignant Tumours Based on Genomic DNA Mutations Data To calculate the Balanced Efficiency Score rating for 105 medicinal products using the Oncobox system, the genome-wide data from the database COSMIC v76 were used (The Catalogue of Somatic Mutations In Cancer) (Forbes et al. 2008), comprising records about 852,964 mutations in 19,491 genes of 1,654 primary malignant liver tumour samples were used. The following medicinal products have gained the top mutation rating (first 10 positions): Regorafenib, Idelalisib, Masitinib, Thalidomide, Sorafenib, Tivantinib, Nintedanib (BIBF 1120), Crizotinib, Foretinib, Flavopiridol (Alvociclib).

Figure 5:
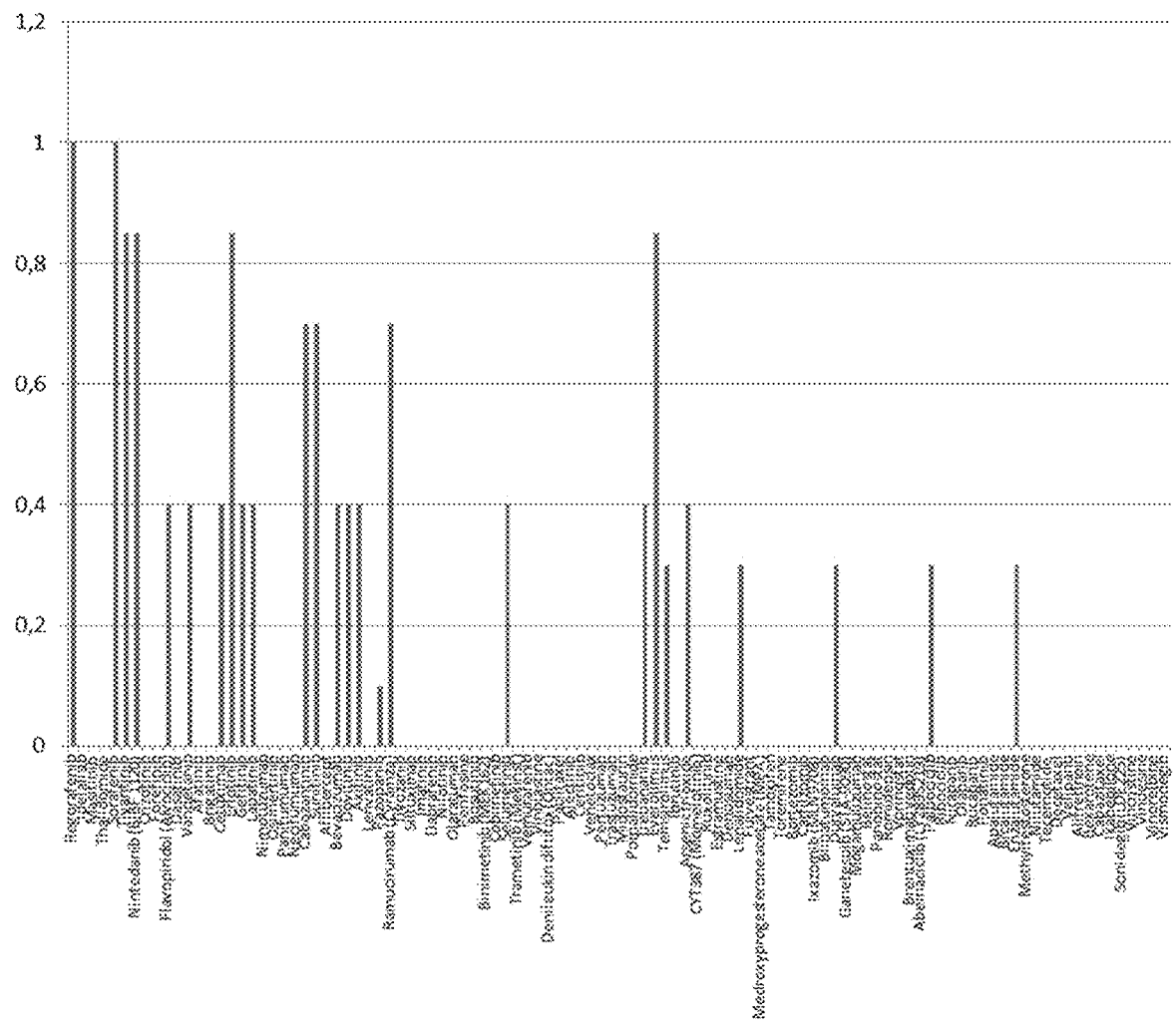
FIG. 5. Clinical status of the drugs selected by BES (Balanced Efficiency Score) values. Clinical significance indices (Y-axis): 1—the drug is approved for clinical use for the given tumour type; 0.85—drug successfully passed phase III clinical trials; 0.7—drug at phase III clinical trials; 0.4—drug successfully passed phase II clinical trials; 0.3—drug at phase II clinical trials; 0.2—drug successfully passed phase Iclinical trials; 0.1—drug at phase I clinical trials.

Among them, Regorafenib was formally accepted for administration in case of liver cancer in routine clinical practice, Tivantinib and Nintedanib (BIBF 1120) passed phase 3 clinical trials, and Flavopiridol (Alvociclib) completed phase 2 clinical trials for liver cancer (www.clinicaltrials.gov). The other drugs having the top Balanced Efficiency Score rating are not currently used for treatments of liver tumours, in case of no clinical trials conducted previously, they may be recommended for review of their potential administration effectiveness for this cancer type. Clinical statuses of all medicinal products sorted according to the Balanced Efficiency Score rating are shown on FIG. 5.

Example 6. Harmonization of Gene Expression Profiles Received Using Different Experimental Platforms with the Oncobox System The expression profiles for the same human mRNA samples were received in the SEQC project using different experimental platforms and published in open databases (Su at al, 2014, SEQC/MAQC-III Consortium, 2014). There were taken the transcription profiles for commercially available human mRNA sample Stratagene Universal Human Reference RNA (UHRR Catalog #740000) using experimental microarray hybridization and deep sequencing platforms: Illumina HiSeq 2000 (GPL11154), Illumina HumanHT-12 V4.0 expression beadchip (GPL10558), Affymetrix Human Gene 2.0 ST Array (GPL17930), Affymetrix GeneChip PrimeView Human Gene Expression Array (GPL16043).

Figure 6:
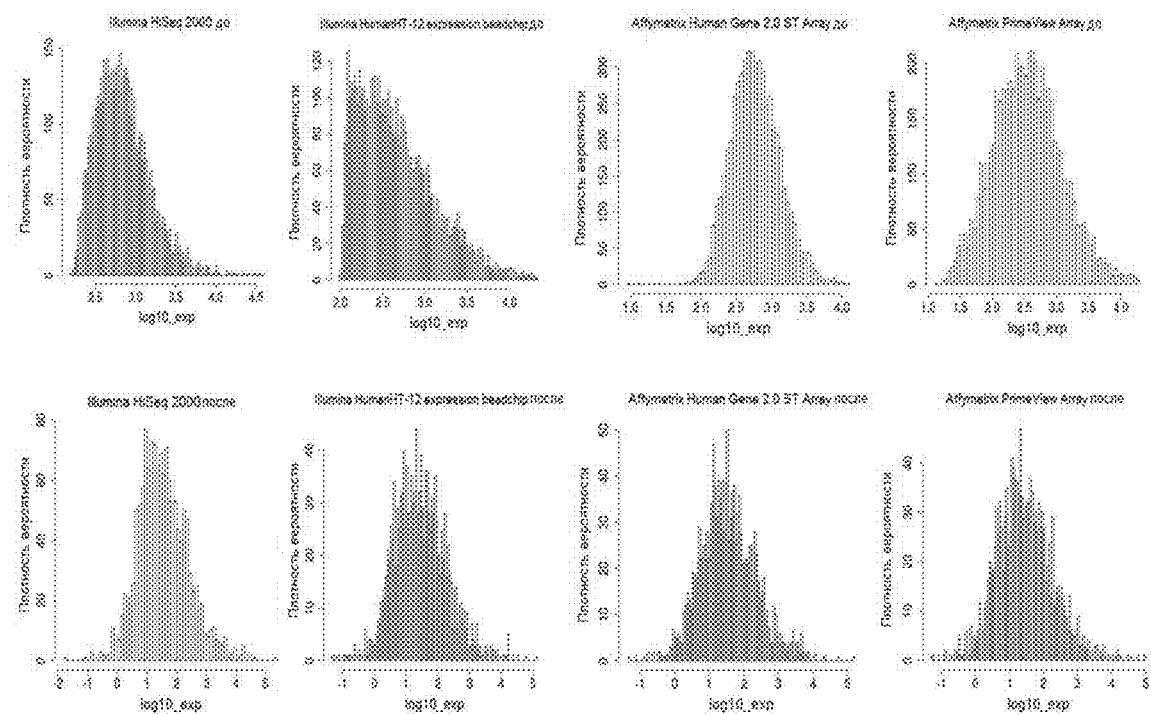
FIG. 6. Bringing the gene expression profile to universal form with the use of Oncobox Shambhala method. Expression profiles before and after harmonization using Shambhala algorithm are shown (upper and lower lines of the panels, respectively). Gene distribution by expression levels is shown (X-axis). Initial expression profiles were obtained for the same biosample (Stratagene Universal Human Reference RNA; UHRR Catalog #740000) using various experimental platforms (from left to right): Illumina HiSeq 2000 (GPL11154), Illumina HumanHT-12 V4.0 expression beadchip (GPL10558), Affymetrix Human Gene 2.0 ST Array (GPL17930) and Affymetrix GeneChip PrimeView Human Gene Expression Array (GPL16043).

In their initial form, the obtained gene expression profiles differed considerably in their expression levels depending on the platform used rather than on the samples types (FIG. 6, top panels). After the application of Shambhala method included in the Oncobox platform, the expression profiles were brought to the standard universal form (FIG. 6, bottom panels).

Example 7. Combination of Mutation and Gene Expression Data for Target Drug Ranking for the Patient with Head and Neck Cancer For an adult oncological patient with stage 4 head and neck cancer, the following line of chemical therapy was selected using the Oncobox platform. For this patient, the tumour tissue biopsy was taken, mRNA expression was profiled and the exome-wide DNA sequencing was performed using Illumina HiSeq 2000 equipment. The amygdala sample taken from a healthy donor for which the gene expression profile was received with the same equipment, was taken as normal tissue sample.

The Balanced drug Efficiency Scores (BES) were calculated for 128 target drugs according to the mRNA expression profiles in tumour and normal samples. Table 5 provides the medicinal products with the highest BES according to the mRNA expression data.

Table 5. Rating of target drugs with the highest BES for the patient with head and neck cancer according to the mRNA expression profiling results.

Simultaneously, BES was calculated for the same patient using the alternative method based on exome-wide sequencing of the same tumour sample. In total, somatic mutations in 13 genes were identified in the patient's tumour. The rating of target drugs according to BES calculated for genomic DNA mutations data is shown on Table 6.

Table 6. Rating of target drugs with the highest BES for the patient with head and neck cancer according to genomic DNA mutation data.

Then, the list of medicinal products which simultaneously had maximum BES values according to the data on genomic DNA mutations and mRNA expression in tumour tissue was generated (Table 7). It was found out that several top drugs had completed phase 3 clinical trials or are recommended by FDA (USA) for head and neck cancer. This evidences in favour of efficiency and reliability of combination of ratings of target drugs calculated for expression and mutation data. According to results obtained, the medicinal product Cetuximab was recommended as the next line of therapy for this patient. The possibility of combining ratings of target drugs based on mRNA and genomic DNA mutation profiles is a unique distinguishing feature of the Oncobox platform.

Table 7. Clinical status of top target drugs having maximum BES ratings according both mRNA and DNA mutation data analyses for the head and neck cancer patient.

Example 8. Comparison of Expression-Based Methods of Ranking Target Drugs: Oncobox Platform Versus Previously Published Approaches Below is the determination of Balanced Efficiency Scores of target drugs calculated using the method of this invention (using the proposed BES) as compared to that previously disclosed in the application US20170193176A1 by the method which uses only molecular pathway activation values for calculation (Drug Score, hereinafter referred to as DS1a).

Determination of target drugs efficiency was made according to transcriptomic profiles of oncology patients from the open database TCGA (The Cancer Genome Atlas), whereupon the efficiency scores were compared with the clinical status of target drugs.

The Cancer Genome Atlas database (TCGA, https://cancergenome.nih.gov/) comprises mutation and transcriptomic profiles of oncology patients with different cancer types. Using the Oncobox system, the Balanced Efficiency Scores (BESs) were calculated for the patients of 11 cancer types (Table 8). For the same group of patients, the target drug efficiency score DS1 was also calculated according to the alternative method previously published in the application US20170193176A1, as well as in the article by Artemov et al., 2015.

Table 8. Statistics of the analysed transcriptomic profiles for patients from the TCGA database by cancer types.

Figure 7:
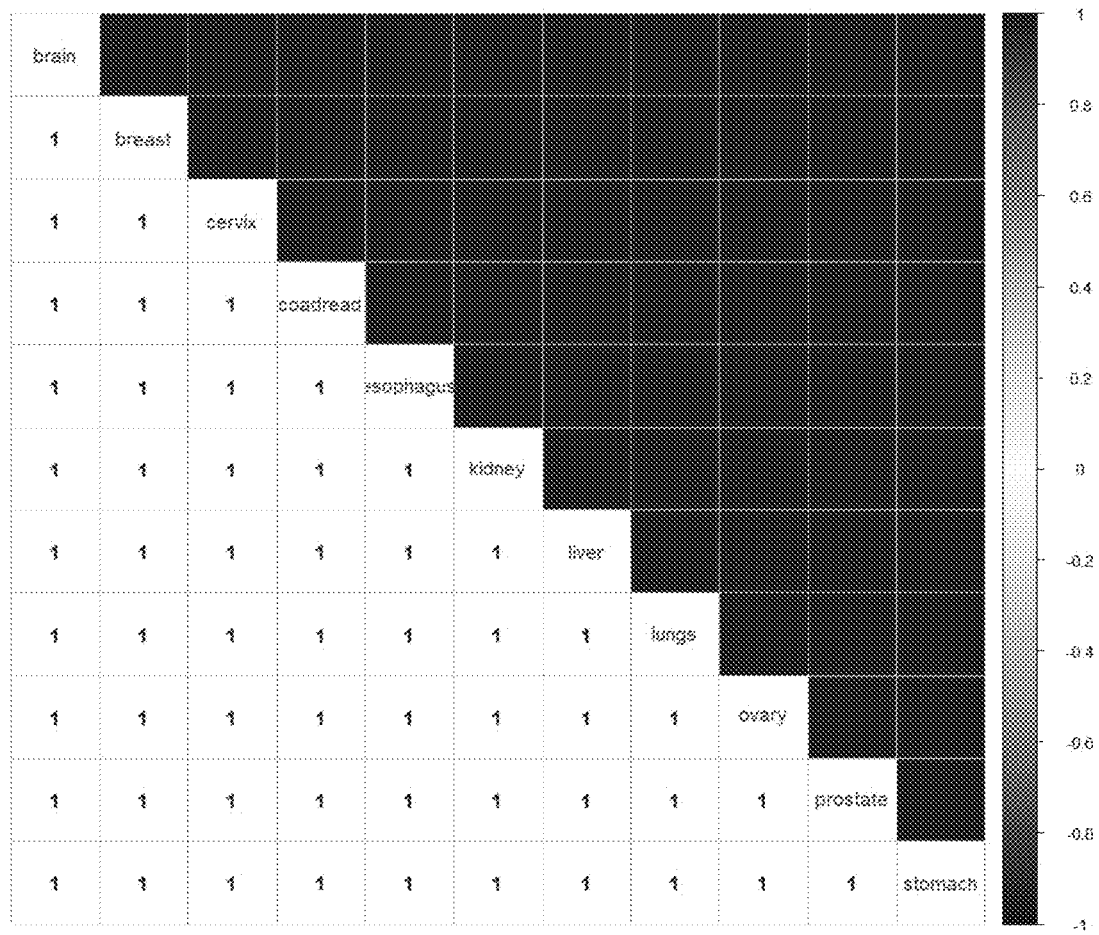
FIG. 7. Jaccard index to compare lists of drugs appearing on the top of the rating based on the DS1 for 11 testing cancer types (shown for disorders indicated by a tissue type).

At the first stage, the target drugs appearing in the top of the rating were analysed separately by BES and by DS1a values. To this end, the above coefficients were calculated for each separate patient's transcriptomic profile. In total, the coefficients for 128 target drugs were analysed. Then, the ratings for the top 10% drugs (top-13 drugs) by BES or DS1a efficiency scores were built. The lists obtained were compared between different cancer types by Jaccard index values. The resulting graph summarizing the paired comparison for all cancer types for DS1a is given in FIG. 7. It can be seen that according to DS1a, top-13 drugs are absolutely the same for different cancer types (wherein, certain positions within the rating may not match). This means that DS1a is not suitable for the personalized prescription of target treatment for oncological patients as according to this rating, most of the patients are supposed to administer the same drugs.

Figure 8:
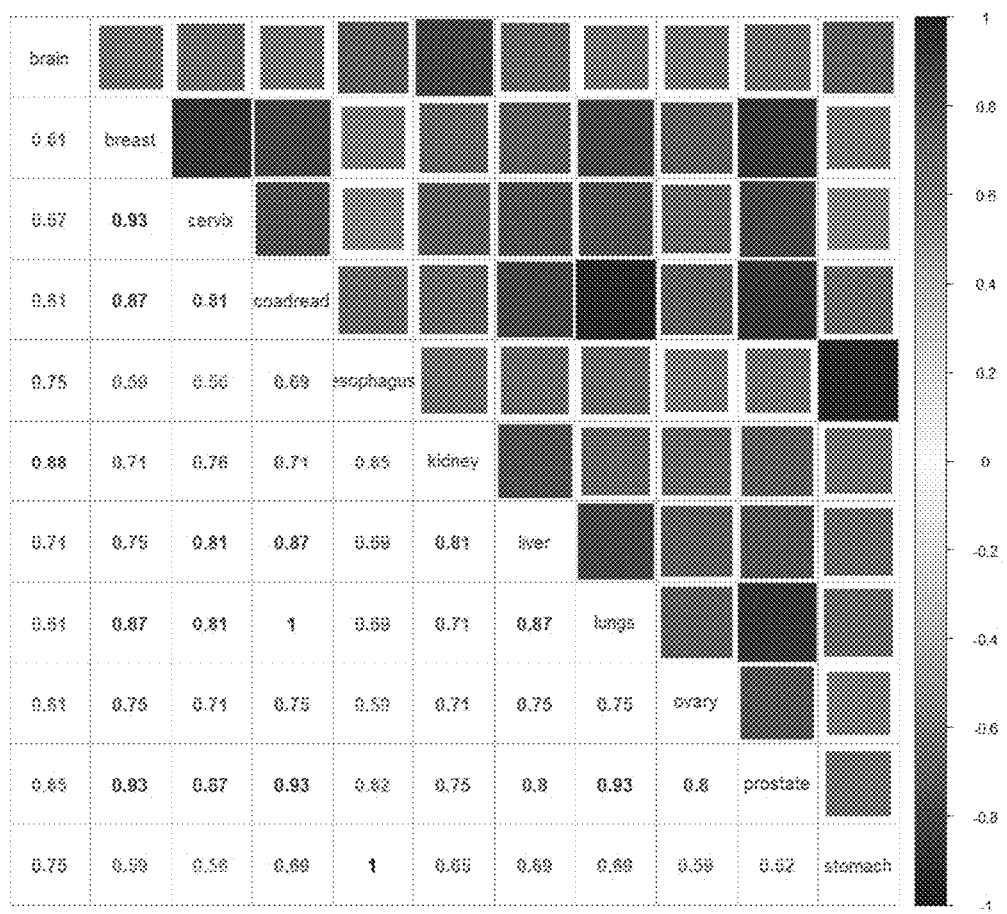
FIG. 8. Jaccard index to compare lists of drugs appearing on the top of the rating that is based on the BES for 11 testing cancer types (shown for disorders indicated by a tissue type).

In parallel, the analogous analysis was done for BES ratings of target drugs. In this case, on the contrary, top-13 positions of drugs varied significantly between the cancer types (FIG. 8), thus reflecting apparently different clinical efficiencies of the target drugs in the different cancer types.

The BES rating, therefore, on the one hand, better corresponded to the clinical data and, on the other hand, was suitable for the personalized prescription of drugs for cancer patients.

It was further established to which extent the rating of target drugs calculated using Oncobox system matches the clinical status of these drugs. To this end, the database clinicaltrials.gov that accumulates information about most of the documented clinical trials related to investigation of target drug efficiencies was taken as the source dataset and was further analysed. The clinical trial stages of 128 target drugs for cervix carcinoma are considered as an example. Depending on the clinical stage of the drug under investigation, it receives a clinical efficiency coefficient varying from 0 to 1 according to the following: 1—the medicinal product is clinically accepted for cervix carcinoma, 0.85—phase 3 of clinical trials completed, 0.7—phase 3 of clinical trials in progress, 0.4—phase 2 of clinical trials, 0.3—phase 1 of clinical trials, and 0—no clinical trials data available. Based on these metrics, it is feasible to calculate to which extent the personalized rating matches the drug clinical status for each particular patient. When the top of the rating contains the medicinal products, which have passed initial phases of clinical trials or even recommended for this cancer type, and the bottom of the rating contains lower proportion of such drugs, it means that the rating reflects the real success rates of the medicinal products.

In order to formalize this principle, the following formula was used:

$$A = \sum_{i=1}^{n_{drugs}} E_i \cdot (\text{rank}(DS_i) - n_{drugs} - 0.5)) \cdot (\sum_{i=1}^{n_{drugs}} E_i)^{-1}$$

where $E_i$—clinical coefficient of the medicinal product i; DS—efficiency score for this target drug, for example, BES or DS1a; $n_{drugs}$—number of target drugs (in this example, 128).

Figure 9:
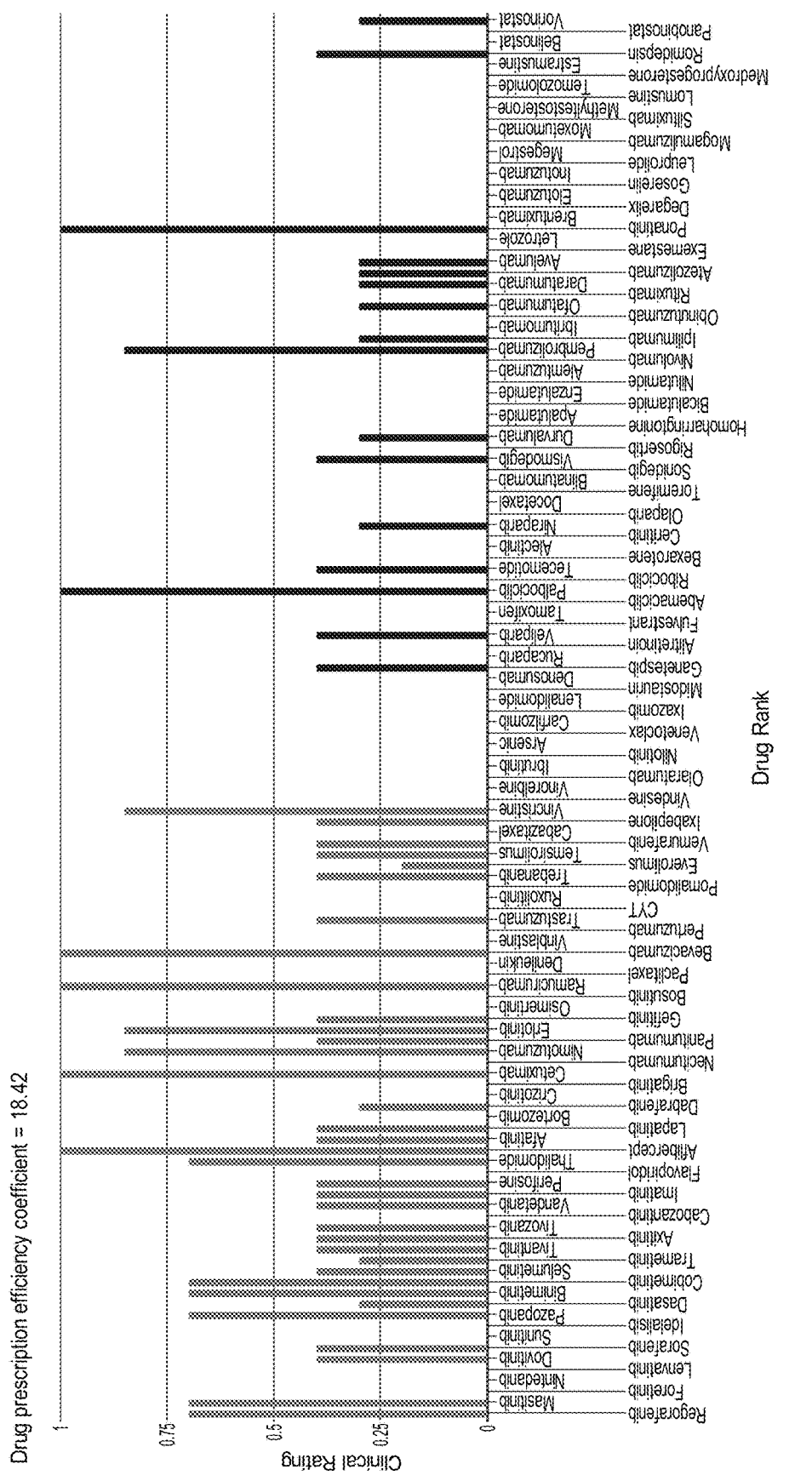
FIG. 9. Comparison of the Oncobox target drugs rating and clinical rating of the same drugs according to the clinicaltrials.gov database (August 2017). The Oncobox drug scoring was based on high throughput transcriptomic profile of a patient with cervical carcinoma extracted from TCGA database Green colour labels drugs appearing in the top of the rating, and red colour—drugs in the bottom of the rating.

The obtained index A called Anubis coefficient assesses if the calculated drug efficiency scores are well matched with their clinical status. FIG. 9 illustrates the graph showing the dependency of BES rating of a drug on its clinical status using the example of one patient with cervix carcinoma. The graph shows that the drugs that were at later stages of clinical trials took top-half positions in the drugs rating. The Anubis coefficient calculated according to the above formula was equal to 14.83 for this patient.

Figure 10:
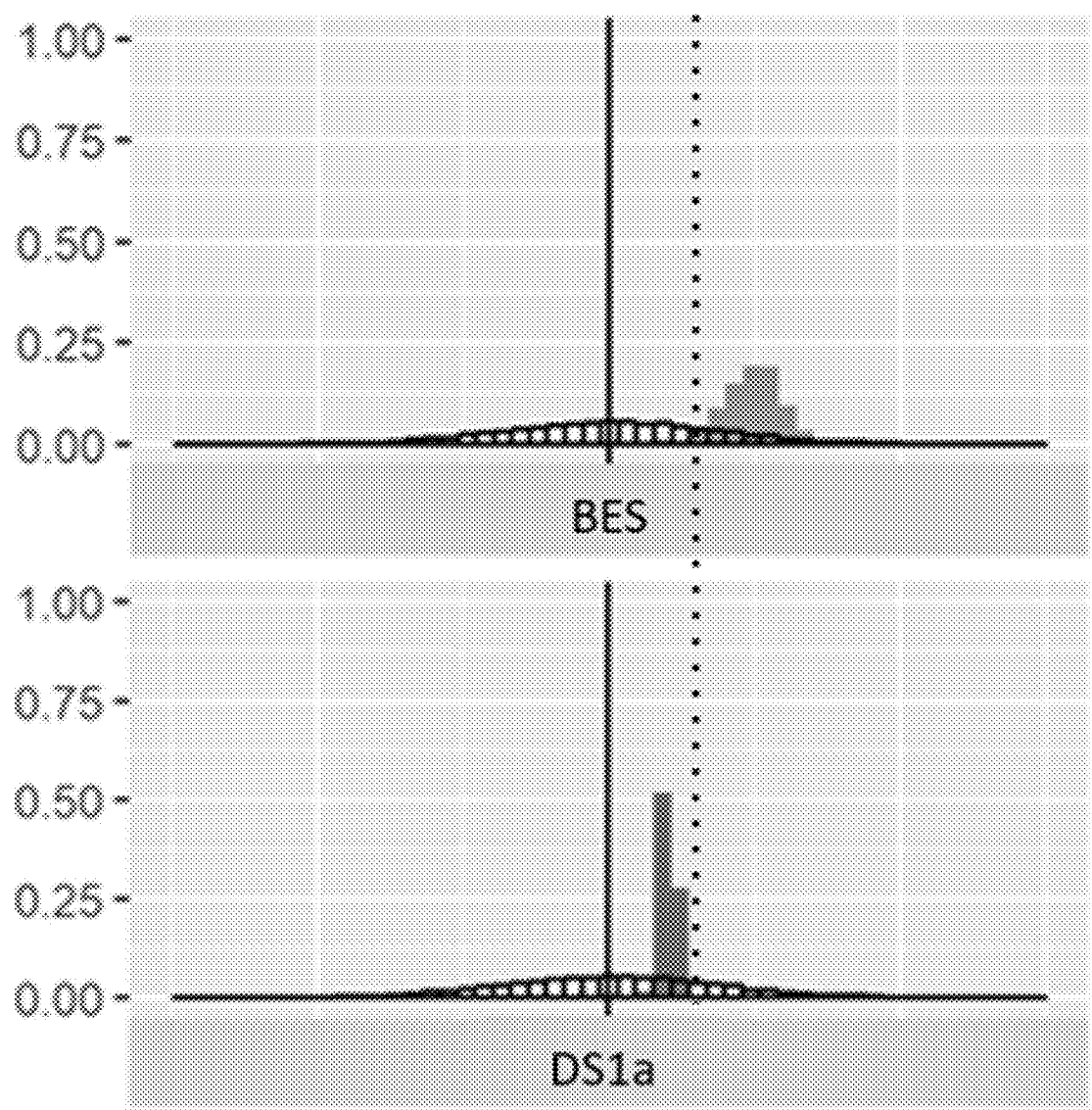
FIG. 10. Density plot of Anubis coefficients calculated by BES (upper graph) or DS1a (lower graph) for 306 patients with cervical carcinoma. Transparent histograms show densities of Anubis coefficients for randomized drugs clinical status.

The Anubis coefficients were next calculated for all patients with cervix carcinoma using BES and DS1a metrics. Density functions of the calculated Anubis coefficients is shown on FIG. 10. The graph demonstrated that in general the Anubis coefficients were significantly higher for BES than for DS1a. This suggests that the BES rating better matches the clinical status of drugs than in case of DS1a. Therefore, BES has a clear advantage over DS1a as the top BES-ranked drugs showed better results in clinical trials.

Irrespective of that the invention is described with the reference to the disclosed embodiments, it should be obvious for the persons skilled in the art that certain detailed description of experiments are given only to illustrate the present invention, and they should be considered as confining the scope of the invention in any way. One would appreciate that the embodiment of different modifications is possible without departing from the spirit of the present invention.

The invention claimed is:

1. A computer-implemented method of defining clinical efficiency of targeted medicinal products selected from a targeted medicinal products group for treatment of a patient with proliferative or oncological disease, the method comprising:
(a) receiving, from a database via a computer interface, information about molecular targets for each targeted medicinal product selected from the group;
(b) taking a patient's tissue sample with proliferative phenotype;
(c) receiving data of at least one type from said sample, where the data type is selected from the following list: (i) genome-wide total mRNA expression data, (ii) genome-wide protein expression data, (iii) genome-wide transcription factor binding site data, (iv) genome-wide mutations data within genomic DNA, (v) genome-wide microRNA expression data;
(d) receiving data from at least one control tissue sample without proliferative phenotype, wherein the control sample is taken from the tissue of the same type as said patient's tissue with proliferative phenotype, and the control sample data type matches the data type received at (c);
(e) receiving data of at least one type on molecular targets for each targeted medicinal product from said patient's sample, wherein the data type is selected from the following list: (i) expression data for mRNAs of said molecular targets, (ii) expression data for said molecular targets, (iii) mutation data for said molecular target genes, (iv) transcription factor binding site data for said molecular target genes, (v) expression data of microRNAs that affect expression of said molecular target genes, wherein each data type (i)-(v) received at (e) matches the data type, respectively (i)-(v), received at (c);
(f) receiving molecular target data for each targeted medicinal product from at least one control tissue sample without proliferative phenotype, wherein the control sample is taken from tissue of the same type as said patient's tissue, and the control sample data type matches the data type received at (e);
(g) defining, via a computer processor, quantitative medicinal product efficiency indicators for each data type (i)-(v) using data received at (c)-(f); and
(h) defining, via the computer processor, clinical efficiency for each targeted medicinal product selected from the targeted medicinal products' group using the average of quantitative efficiency indicators defined at (g).

2. The method according to claim 1, wherein the data received from at least one control tissue sample are harmonized with the data received at (c) and (e).

3. The method according to claim 2, wherein:
at (c), data of at least two types are received;
at (g), quantitative medicinal product efficiency indicators are individually calculated for each said data type; and
clinical efficiency for each targeted medicinal product selected from the targeted medicinal products' group are defined by averaging said quantitative efficiency indicators calculated for each data type.

4. The method according to claim 3, wherein at(c), genome-wide protein expression data and genome-wide mutations data within genomic DNA are received.

5. A method of treatment a patient with proliferative or oncological disease, the method comprising:
receiving information about available targeted medicinal products and forming a targeted medicinal products' group;
using the method of claim 1, having defined the clinical efficiency of the targeted medicinal products selected from the targeted medicinal products' group; and
selecting the medicinal product for the patient that has the best or one of the best defined quantitative efficiency indicators.

6. A clinical efficiency ranging system for targeted medicinal products selected from a targeted medicinal products' group used for a patient with proliferative or oncological disease, the system comprising:
at least one processor; and
at least one memory that contains machine-readable instructions, which, when executed by the at least one processor, define the clinical efficiencies of said targeted medicinal products using the computer implemented operations comprising:
(a) receiving, from a database via a computer interface, information about molecular targets for each targeted medicinal product selected from the group;
(c) receiving data of at least one type from a tissue sample with proliferative phenotype obtained from said patient, where the data type is selected from the following list: (i) genome-wide total mRNA expression data, (ii) genome-wide protein expression data, (iii) genome-wide transcription factor binding site data, (iv) genomewide mutations data within genomic DNA, (v) genome-wide microRNA expression data;
(d) receiving data from at least one control tissue sample without proliferative phenotype, wherein the control sample is taken from the tissue of the same type as said patient's tissue with proliferative phenotype, and the control sample data type matches the data type received at (c);
(e) receiving data of at least one type on molecular targets for each targeted medicinal product from said patient's sample, wherein the data type is selected from the following list: (i) expression data for mRNAs of said molecular targets, (ii) expression data for said molecular targets, (iii) mutation data for said molecular target genes, (iv) transcription factor binding site data for said molecular target genes, (v) expression data of microRNAs that affect expression of said molecular target genes, wherein each data type (i)-(v) received at (e) matches the data type, respectively (i)-(v), received at (c);
(f) receiving molecular target data for each targeted medicinal product from at least one control tissue sample without proliferative phenotype, wherein the control sample is taken from tissue of the same type as said patient's tissue, and the control sample data type matches the data type received at (e);
(g) defining quantitative medicinal product efficiency indicators for each data type (i)-(v) using data received at (c)-(f); and
(h) defining clinical efficiency for each targeted medicinal product selected from the targeted medicinal products' group using the average of quantitative efficiency indicators defined at (g).

7. The system according to claim 6, wherein the data received from at least one control tissue sample are harmonized with the data received at (c) and (e).

8. The system according to claim 7, wherein:
at (c), data of at least two types are received;
at (g), quantitative medicinal product efficiency indicators are individually calculated for each said data type; and
clinical efficiency for each targeted medicinal product selected from the targeted medicinal products' group are defined by averaging said quantitative efficiency indicators calculated for each data type.

9. The system according to claim 8, wherein at (c), genome-wide protein expression data and genome-wide mutations data within genomic DNA are received.

10. A computer-implemented method of defining clinical efficiency of targeted medicinal products selected from a targeted medicinal products group for treatment of a patient with proliferative or oncological disease, the method comprising:
   (a) receiving, from a first database via a first computer interface, information about molecular targets for each targeted medicinal product selected from the group;
   (b) taking a patient's tissue sample with proliferative or oncological phenotype;
   (c) receiving data of at least one type from said sample, where the data type is selected from the following list: (i) genome-wide total mRNA expression data, (ii) genome-wide protein expression data, (iii) genome-wide transcription factor binding site data, (iv) genome-wide mutations data within genomic DNA, (v) genome-wide microRNA expression data;
   (d) receiving data from at least one control tissue sample without proliferative phenotype, wherein the control sample is taken from the tissue of the same type as said patient's tissue with proliferative or oncological phenotype, and the control sample data type matches the data type received at (c);
   (e) receiving, from a second database via a second computer interface, data of at least one type on molecular targets for each targeted medicinal product from said patient's sample, wherein the data type is selected from the following list: (i) expression data for mRNAs of said molecular targets, (ii) expression data for said molecular targets, (iii) mutation data for said molecular target genes, (iv) transcription factor binding site data for said molecular target genes, (v) expression data of microRNAs that affect expression of said molecular target genes, wherein each data type (i)-(v) received at (e) matches the data type, respectively (i)-(v), received at (c);
   (f) receiving, from the second database via the second computer interface, molecular target data for each targeted medicinal product from at least one control tissue sample without proliferative phenotype, wherein the control sample is taken from tissue of the same type as said patient's tissue, and the control sample data type matches the data type received at (e);
   (g) defining, via a computer processor, quantitative medicinal product efficiency indicators for each data type (i)-(v) using data received at (c)-(f), including performing a preprocessing operation on gene expression mRNA and gene expression protein related data in accordance with a predefined data harmonization algorithm provided that at least two different technology platforms are used to gather the gene expression mRNA related data and the gene expression protein related data, the preprocessing being performable by the computer processor prior to joining the gene expression mRNA related data and the gene expression protein related data with control sample derived data, the predefined data harmonization algorithm being programmed to transform into a common form at least the gene expression mRNA and gene expression protein related data, the common form permitting the computer processor to make programmatic comparisons between at least the gene expression mRNA and gene expression protein related data regardless of the technology platform(s) used to obtain at least the gene expression mRNA and gene expression protein related data; and
   (h) outputting, via the computer processor, clinical efficiency scores for each targeted medicinal product selected from the targeted medicinal products' group using the average of quantitative efficiency indicators defined at (g).

11. The method according to claim 10, wherein the predefined data harmonization algorithm comprises, via the computer processor:
   adding gene expression sample profiles to an auxiliary calibration set of profiles using quantile normalization;
   converting the auxiliary calibration set of profiles into a form that is characteristic for a set of standard expression profiles via piecewise harmonization.

12. The method according to claim 10, wherein (g) includes combining data regarding different molecular data types.

13. The method according to claim 10, wherein the clinical efficiency scores are generated based on molecular pathway activation level data, and relative expression or mutation burden data, pertaining to genes.

14. The method according to claim 10, further comprising automatically annotating molecular pathways.

* * * * *